United States Patent [19]

Takaya et al.

[11] Patent Number: 4,546,101
[45] Date of Patent: Oct. 8, 1985

[54] NEW CEPHEM COMPOUNDS USEFUL FOR TREATING INFECTIOUS DISEASES IN HUMAN BEING AND ANIMALS AND PROCESSES FOR PREPARATION THEREOF

[75] Inventors: Takao Takaya, Kawanishi; Hisashi Takasugi, Hamagutinishi; Hideaki Yamanaka, Hirakata; Kenji Miyai, Kawanishi; Yoshikazu Inoue, Amagasaki, all of Japan

[73] Assignee: Fujisawa Pharmaceutical Co., Ltd., Osaka, Japan

[21] Appl. No.: 528,796

[22] Filed: Sep. 2, 1983

[30] Foreign Application Priority Data

Sep. 10, 1982 [GB] United Kingdom ............... 8225836
Apr. 29, 1983 [GB] United Kingdom ............... 8311815

[51] Int. Cl.$^4$ .................. A61K 31/54; C07D 501/00; C07D 501/14
[52] U.S. Cl. .................. 514/253; 514/338; 544/22; 544/24; 544/25; 260/691
[58] Field of Search ............... 544/24, 22; 424/246

[56] References Cited

U.S. PATENT DOCUMENTS 4,423,213 12/1983 Takaya et al. ............ 544/22
4,444,773 4/1984 Donia et al. ............. 544/282

OTHER PUBLICATIONS

Takaya et al, Chem. Abst. 101:38270e.
Takaya et al, Chem. Abst. 101:6933g.
Rhone-Poulenc Industries, Chem. Abst. 96:52078h.
Yamanouchi Pharm. Chem. Abst. 96:122518c.
Faye et al, Chem. Abst. 95:7308b.
Faye et al, Chem. Abst. 95:97816t.
Beattie et al, Chem. Abst. 95:132922y.
Rhone-Poulenc Industries, Chem. Abst. 95:50683a.
Faye et al, Chem. Abst. 95:187274u.
Beattie et al, Chem. Abst. 86:5480s.
Weir et al, Chem. Abst. 82:43442f.
Cristensen et al, Chem. Abst. 81:49691n.

Primary Examiner—Donald G. Daus
Assistant Examiner—Cecilia Shen
Attorney, Agent, or Firm—Oblon, Fisher, Spivak, McClelland & Maier

[57] ABSTRACT

The invention relates to cephem compounds of high antimicrobial activity of the formula:

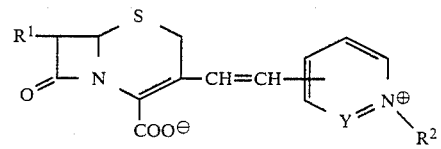

wherein
$R^1$ is amino or acylamino,
$R^2$ is lower alkyl, and
Y is CH or N.

12 Claims, No Drawings

NEW CEPHEM COMPOUNDS USEFUL FOR TREATING INFECTIOUS DISEASES IN HUMAN BEING AND ANIMALS AND PROCESSES FOR PREPARATION THEREOF

The present invention relates to new cephem compounds and pharmaceutically acceptable salts thereof. More particularly, it relates to new cephem compounds and pharmaceutically acceptable salts thereof, which have antimicrobial activities, to processes for preparation thereof, to pharmaceutical composition comprising the same, and to a method of using the same therapeutically for the treatment of infectious diseases in human being and animals.

Accordingly, it is one object of the present invention to provide new cephem compounds and pharmaceutically acceptable salts thereof, which are highly active against a number of pathogenic microorganisms.

Another object of the present invention is to provide processes for the preparation of new cephem compounds and pharmaceutically acceptable salts thereof.

A further object of the present invention is to provide pharmaceutical composition comprising, as active ingredients, said new cephem compounds and pharmaceutically acceptable salts thereof.

Still further object of the present invention is to provide a method for the treatment of infectious diseases caused by pathogenic bacteria in human being and animals.

The object new cephem compounds are novel and can be represented by the following general formula (I):

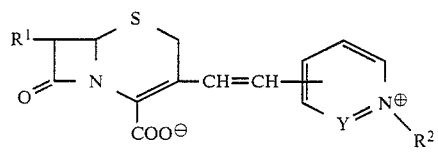

wherein
$R^1$ is amino or acylamino,
$R^2$ is lower alkyl, and
Y is CH or N.

According to the present invention, the new cephem compounds (I) can be prepared by various processes which are illustrated in the following schemes.

Process 1

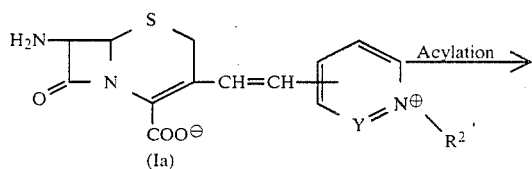

(Ia)
or its reactive derivative
at the amino group
or a salt thereof $\xrightarrow{\text{Acylation}}$ Process 1

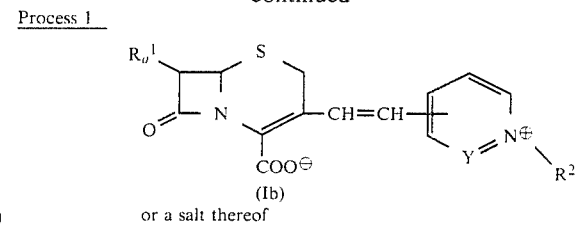

(Ib)
or a salt thereof

Process 2

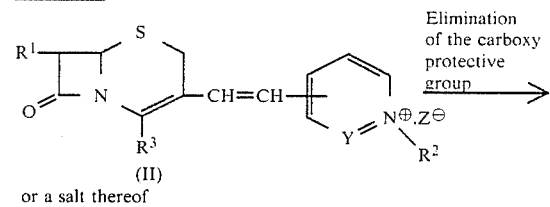

(II)
or a salt thereof $\xrightarrow{\text{Elimination of the carboxy protective group}}$

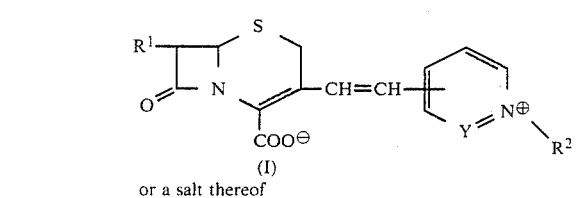

(I)
or a salt thereof

Process 3

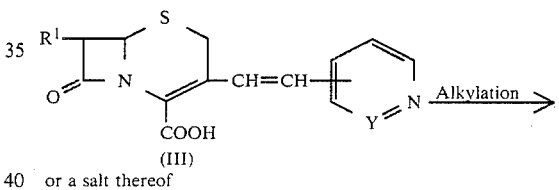

(III)
or a salt thereof $\xrightarrow{\text{Alkylation}}$

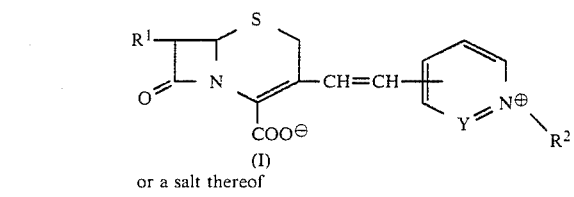

(I)
or a salt thereof

Process 4

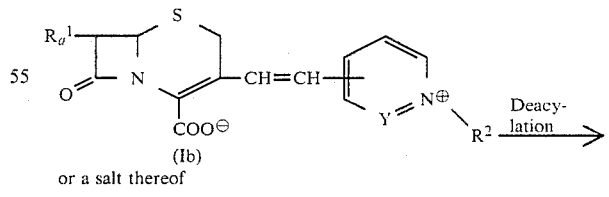

(Ib)
or a salt thereof $\xrightarrow{\text{Deacylation}}$

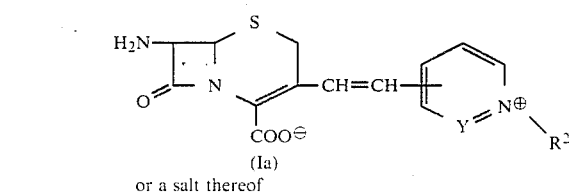

(Ia)
or a salt thereof

Process 5

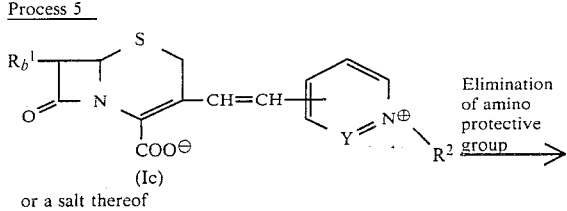

(Ic) or a salt thereof

Elimination of amino protective group →

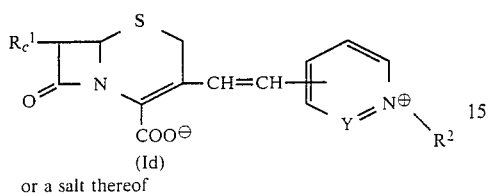

(Id) or a salt thereof wherein
R$^1$, R$^2$ and Y are each as defined above,
R$_a^1$ is acylamino,
R$_b^1$ is acylamino having protected amino,
R$_c^1$ is acylamino having amino,
R$^3$ is a protected carboxy, and
Z is an acid residue.

Among the starting compounds in the present invention, the compounds (II) and (III) are novel and can be prepared by the processes which are illustrated in the following schemes.

Process A

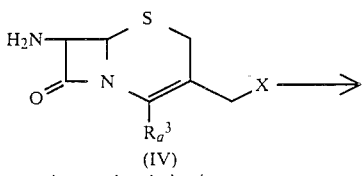

(IV) or its reactive derivative at the amino group or a salt thereof

Process A

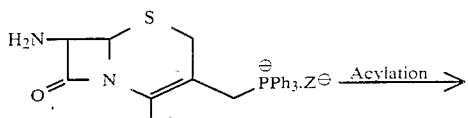

(V) or its reactive derivative at the amino group or a salt thereof

Acylation →

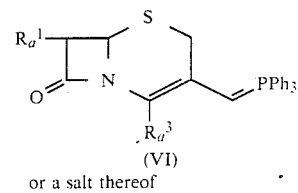

(VI) or a salt thereof

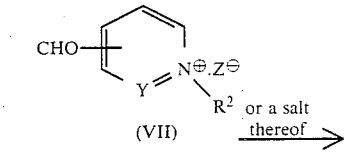

(VIa) or a salt thereof

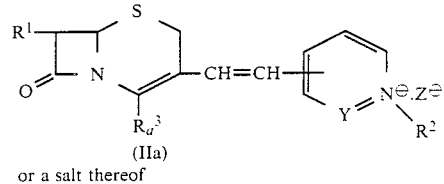

(VII) or a salt thereof →

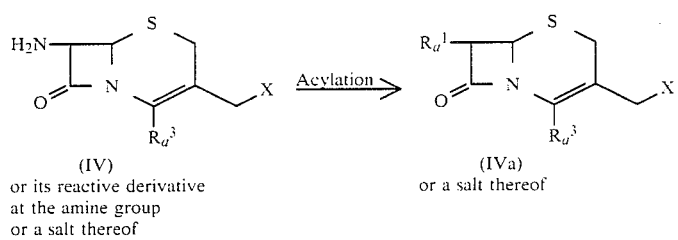

(IIa) or a salt thereof

Process B - (1)

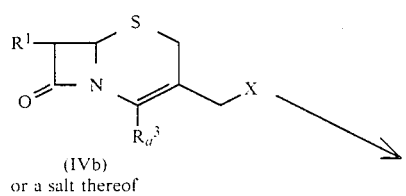

(IV) or its reactive derivative at the amino group or a salt thereof

Acylation →

(IVa) or a salt thereof (IVb) or a salt thereof

Process B - (1)
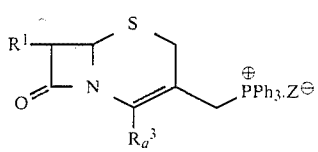
(Va)
or a salt thereof
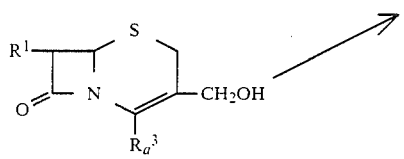
(VIII)
or its reactive derivative
at the hydroxymethyl group
or a salt thereof
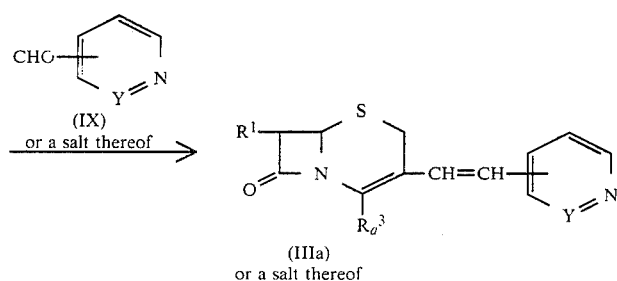
(IIIa)
or a salt thereof
Process B - (2)
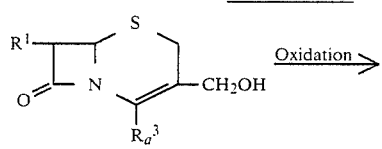
(VIII)
or its reactive derivative
at the hydroxymethyl group
or a salt thereof
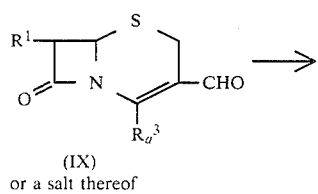
(IX)
or a salt thereof
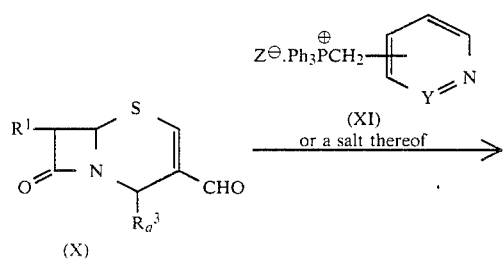
(X)
or a salt thereof
-continued
Process B - (2)
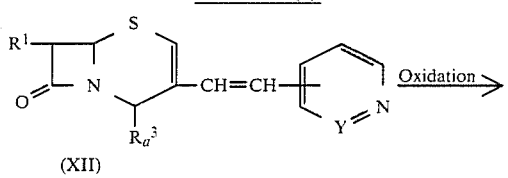
(XII)
or a salt thereof
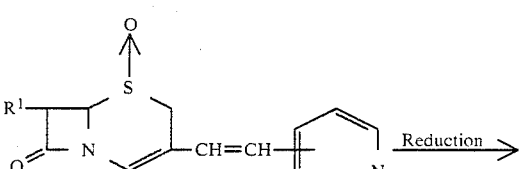
(XIII)
or a salt thereof
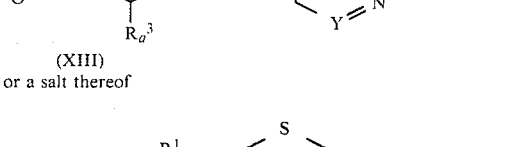
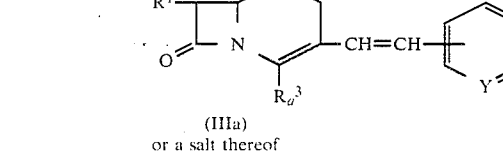
(IIIa)
or a salt thereof Process B - (3)

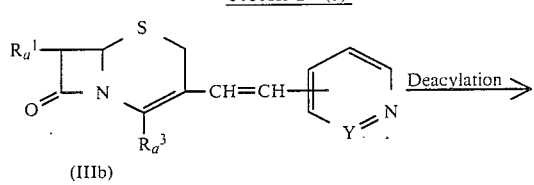

(IIIb) or a salt thereof

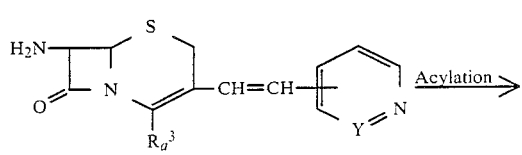

(IIIc) or its reactive derivative at the amine group or a salt thereof

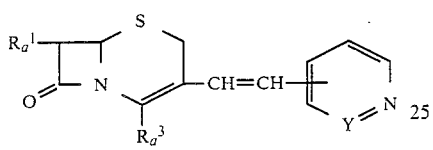

(IIIb) or a salt thereof

Process B - (4)

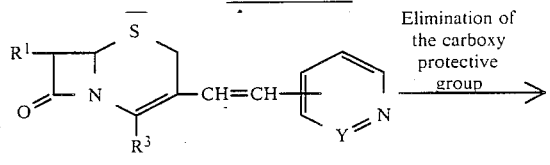

(IIId) or a salt thereof

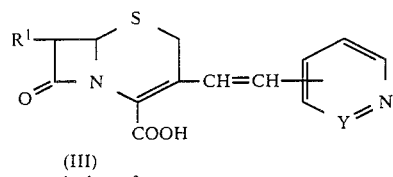

(III) or a salt thereof

Process B - (5)

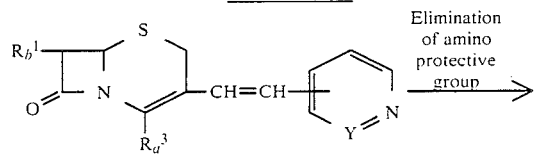

(IIIe) or a salt thereof

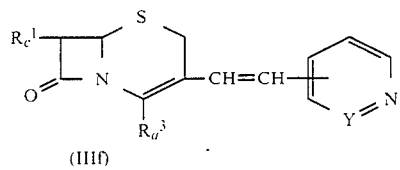

(IIIf) or a salt thereof wherein, $R^1$, $R_a^1$, $R_b^1$, $R_c^1$, $R^2$, $R^3$, Y and Z are each as defined above, $R_a^3$ is carboxy or a protected carboxy, X is halogen, and Ph is phenyl.

Regarding the object compounds (I), (Ia) to (Id) and the starting compounds (II), (IIa), (III), (IIIa), (IIIb), (IIIc), (IIId), (IIIe), (IIIf), (VI), (VIa), (XII) and (XIII), it is to be understood that said object and starting compounds include cis isomer, trans isomer and a mixture thereof. For example, with regard to the object compound (I), cis isomer means one geometrical isomer having the partial structure represented by the following formula:

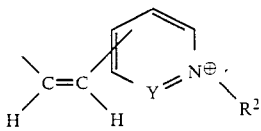

(wherein $R^2$ and Y are each as defined above) and trans isomer means the other geometrical isomer having the partial structure represented by the following formula:

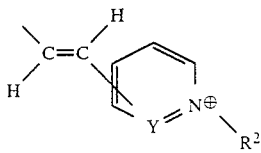

(wherein $R^2$ and Y are each as defined above).

Suitable pharmaceutically acceptable salts of the object compounds (I) are conventional non-toxic salts and include an organic acid salt (e.g. acetate, maleate, tartrate, methanesulfonate, benzenesulfonate, formate, toluenesulfonate, trifluoroacetate, etc.), an inorganic acid salt (e.g. hydrochloride, hydriodide, sulfate, phosphate, etc.), a salt with an amino acid (e.g. arginine, aspartic acid, glutamic acid, etc.), and the like.

In the above and subsequent descriptions of the present specification, suitable examples and illustrations of the various definitions which the present invention include within the scope thereof are explained in detail as follows.

The term "lower" is intended to mean 1 to 6 carbon atom(s), unless otherwise indicated.

Suitable "acyl" and "acyl moiety" in the term "acylamino" as mentioned above may include carbamoyl, aliphatic acyl group and acyl group containing an aromatic ring, which is referred to as aromatic acyl, or heterocyclic ring, which is referred to as heterocyclic acyl.

Suitable example of said acyl may be illustrated as follows:

Aliphatic acyl such as lower or higher alkanoyl (e.g. formyl, acetyl, succinyl, hexanoyl, heptanoyl, valeryl, stearoyl, etc.);

lower or higher alkoxycarbonyl (e.g. methoxycarbonyl, ethoxycarbonyl, t-butoxycarbonyl, t-pentyloxycarbonyl, heptyloxycarbonyl, etc.);

lower or higher alkanesulfonyl (e.g. methanesulfonyl, ethanesulfonyl, etc.); or the like;

Aromatic acyl such as aroyl (e.g. benzoyl, toluoyl, naphthoyl, etc.);

ar(lower)alkanoyl such as phenyl(lower)alkanoyl (e.g. phenylacetyl, phenylpropionyl, etc.);

aryloxycarbonyl (e.g. phenoxycarbonyl, naphthyloxycarbonyl, etc.);
aryloxy(lower)alkanoyl (e.g. phenoxyacetyl, phenoxypropionyl, etc.);
arylglyoxyloyl (e.g. phenylglyoxyloyl, naphthylglyoxyloyl, etc.);
arenesulfonyl (e.g. benzenesulfonyl, p-toluenesulfonyl, etc.); or the like;
Heterocyclic acyl such as
heterocycliccarbonyl (e.g. thenoyl, furoyl, nicotinoyl, etc.);
heterocyclic(lower)alkanoyl (e.g. thienylacetyl, thiazolylacetyl, thiadiazolylacetyl, tetrazolylacetyl, etc.);
heterocyclicglyoxyloyl (e.g. thiazolylglyoxyloyl, thienylglyoxyloyl, etc.); or the like; in which suitable heterocyclic moiety in the terms "heterocycliccarbonyl", "heterocyclic(lower)alkanoyl" and "heterocyclicglyoxyloyl" as mentioned above means, in more detail, saturated or unsaturated, monocyclic or polycyclic heterocyclic group containing at least one hetero-atom such as an oxygen, sulfur, nitrogen atom and the like.

And, especially preferable heterocyclic group may be heterocyclic group such as unsaturated 3 to 8-membered more preferably 5 or 6-membered heteromonocyclic group containing 1 to 4-nitrogen atom(s), for example, pyrrolyl, pyrrolinyl, imidazolyl, pyrazolyl, pyridyl and its N-oxide, dihydropyridyl, pyrimidyl, pyrazinyl, pyridazinyl, triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), etc.;

saturated 3 to 8-membered (more preferably 5 or 6-membered)heteromonocyclic group containing 1 to 4 nitrogen atom(s), for example, pyrrolidinyl, imidazolidinyl, piperidino, piperazinyl, etc.;

unsaturated condensed heterocyclic group containing 1 to 4 nitrogen atom(s), for example, indolyl, isoindolyl, indolizinyl, benzimidazolyl, quinolyl, isoquinolyl, indazolyl, benzotriazolyl, etc.;

unsaturated 3 to 8-membered (more preferably 5 or 6-membered) heteromonocyclic group containing 1 to 2 oxygen atom(s) and 1 to 3 nitrogen atom(s), for example, oxazolyl, isoxazolyl, oxadiazolyl (e.g. 1,2,4-oxadiazolyl, 1,3,4-oxadiazolyl, 1,2,5-oxadiazolyl, etc.) etc.;

saturated 3 to 8-membered (more preferably 5 or 6-membered) heteromonocyclic group containing 1 to 2 oxygen atom(s) and 1 to 3 nitrogen atom(s), for example, morpholinyl, sydnonyl, etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered (more preferably 5 or 6-membered) heteromonocyclic group containing 1 to 2 sulfur atom(s) and 1 to 3 nitrogen atom(s), for example, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.), dihydrothiazinyl, etc.;

saturated 3 to 8-membered (more preferably 5 or 6-membered) heteromonocyclic group containing 1 to 2 sulfur atom(s) and 1 to 3 nitrogen atom(s), for example, thiazolidinyl, etc.;

unsaturated 3 to 8-membered (more preferably 5 or 6-membered) heteromonocyclic group containing 1 to 2 sulfur atom(s), for example, thienyl, dihydrodithiinyl, dihydrodithiolyl, etc.;

unsaturated condensed heterocyclic group containing 1 to 2 sulfur atom(s) and 1 to 3 nitrogen atom(s), for example, benzothiazolyl, benzothiadiazolyl, etc.; unsaturated 3 to 8-membered (more preferably 5 to 6-membered) heteromonocyclic group containing an oxygen atom, for example, furyl, etc.;

unsaturated 3 to 8-membered (more preferably 5 or 6-membered) heteromonocyclic group containing an oxygen atom and 1 to 2 sulfur atom(s), for example, dihydrooxathiinyl, etc.;

unsaturated condensed heterocyclic group containing 1 to 2 sulfur atom(s), for example, benzothienyl, benzodithiinyl, etc.;

unsaturated condensed heterocyclic group containing an oxygen atom and 1 to 2 sulfur atom(s), for example, benzoxathiinyl, etc. and the like.

As to the heterocyclic group as mentioned above, the following points are to be noted. That is, in case that the heterocyclic group is specifically thiazolyl or thiadiazolyl group having amino or protected amino as a substituent in its molecule, said thiazolyl or thiadiazolyl group include tautomeric isomers, which are caused by the specific behavior of the thiazole or thiadiazole ring. That is, for example, said amino- or protected aminothiazolyl or thiadiazolyl group is represented by the formula:

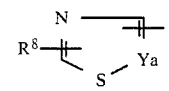

(A) (wherein $R^8$ is amino or protected amino and Ya is CH or N), and in case that the group of the formula (A) takes the formula:

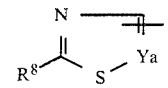

(A') (wherein $R^8$ and Ya are each as defined above), said group of the formula (A') can also be alternatively represented by its tautomeric formula:

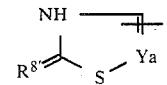

(A") (wherein Ya is as defined above and $R^{8'}$ is imino or protected imino). That is, both of the said groups of the formulae (A') and (A") are in the state of tautomeric equilibrium which can be represented by the following equilibrium:

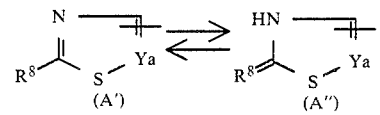

(wherein $R^8$, Ya and $R^{8'}$ are each as defined above).

These types of tautomerism between 2-aminothiazole or thiadiazole compounds and 2-iminothiazoline or thiadiazoline compounds as stated above have been well known in the arts, and it is obvious to a person skilled in arts that both of the tautomeric isomers are equilibrated and lie in the reciprocally convertible state, and accordingly it is to be understood that such isomers are included within the same category of the compound per se. Accordingly, the both of the tautomeric forms are clearly included within the scope of the present invention. In the present specification, the object and starting compounds including the group of such tautomeric isomers are represented by using one of the expressions therefor, i.e. 2-amino(or protected amino)thiazolyl or thiadiazolyl and the formula:

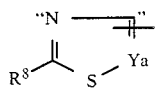

only for the convenient sake. The acyl moiety as stated above may have one to ten, same or different, suitable substituent(s) such as lower alkyl (e.g. methyl, ethyl, etc.); lower alkoxy (e.g. methoxy, ethoxy, propoxy, etc.); lower alkylthio (e.g., methylthio, ethylthio, etc.); lower alkylamino (e.g. methylamino, etc.); cyclo(lower)alkyl (e.g. cyclopentyl, cyclohexyl, etc.); cyclo(lower)alkenyl (e.g. cyclohexenyl; cyclohexadienyl, etc.); halogen; amino; protected amino; hydroxy; protected hydroxy; cyano; nitro; carboxy; protected carboxy; sulfo; sulfamoyl; imino; oxo; amino(lower)alkyl (e.g. aminomethyl, aminoethyl, etc.); carbamoyloxy; a group of the formula: $=N-OR^9$ wherein $R^9$ is hydrogen, lower alkyl (e.g. methyl, ethyl, propyl, etc.), lower alkenyl (e.g. vinyl, allyl, 2-butenyl, etc.), lower alkynyl (e.g. ethynyl, 2-propynyl, etc.), cyclo(lower)alkyl (e.g. cyclopropyl, cyclohexyl, etc.), ar(lower)alkyl such as phenyl(lower)alkyl (e.g. benzyl, phenethyl, etc.), carboxy(lower)alkyl (e.g. carboxymethyl, 1-carboxyethyl, etc.), protected carboxy(lower)alkyl or the like.

In this connection, when the acyl moiety has a group of the formula: $=N-OR^9$, wherein $R^9$ is as defined above, as substituent(s), there are geometrical isomers (syn and anti isomers) due to the presence of double bond. And, for example, the syn isomer means one geometrical isomer having the group of the formula:

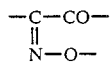

and the corresponding anti isomer means the other geometrical isomer having the group of the formula:

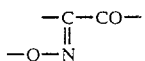

Suitable "protected amino" may include acylamino wherein "acyl" moiety can be referred to the ones as mentioned above, phosphonoamino, protected phosphonoamino, ar(lower)alkylamino such as benzylamino, phenethylamino, tritylamino; and the like.

Suitable "protected phosphono" may include esterified phosphono in which said ester may be the ones such as lower alkyl ester (e.g. methyl ester, ethyl ester, propyl ester, isopropyl ester, butyl ester, isobutyl ester, t-butyl ester, pentyl ester, t-pentyl ester, hexyl ester, etc.) or the like.

Suitable "protected hydroxy" may include acyloxy wherein "acyl" moiety can be referred to the ones as mentioned above.

Suitable "protected carboxy" and "protected carboxy moiety" in the term "protected carboxy(lower)alkyl" may include esterified carboxy wherein "esterified carboxy" can be referred to the ones as mentioned below.

Suitable examples of the ester moiety of an esterified carboxy may be the ones such as lower alkyl ester (e.g. methyl ester, ethyl ester, propyl ester, isopropyl ester, butyl ester, isobutyl ester, tert-butyl ester, pentyl ester, hexyl ester, 1-cyclopropylethyl ester, etc.) which may have at least one suitable substituent(s), for example, lower alkanoyloxy(lower)alkyl ester [e.g. acetoxymethyl ester, propionyloxymethyl ester, butyryloxymethyl ester, valeryloxymethyl ester, pivaloyloxymethyl ester, hexanoyloxymethyl ester, 1(or 2)-acetoxyethyl ester, 1(or 2 or 3)-acetoxypropyl ester, 1(or 2 or 3 or 4)-acetoxybutyl ester, 1(or 2)-propionyloxyethyl ester, 1(or 2 or 3)-propionyloxypropyl ester, 1(or 2)-butyryloxyethyl ester, 1(or 2)-isobutyryloxyethyl ester, 1(or 2)-pivaloyloxyethyl ester, 1(or 2)-hexanoyloxyethyl ester, isobutyryloxymethyl ester, 2-ethybutyryloxymethyl ester, 3,3-dimethylbutyryloxymethyl ester, 1(or 2)-pentanoyloxyethyl ester, etc.] lower alkanesulfonyl(lower)alkyl ester (e.g. 2-mesylethyl ester, etc.), mono(or di or tri)-halo(lower)alkyl ester (e.g. 2-iodoethyl ester, 2,2,2-trichloroethyl ester, etc.), lower alkoxycarbonyloxy(lower)alkyl ester (e.g. methoxycarbonyloxymethyl ester, ethoxycarbonyloxymethyl ester, 2-methoxycarbonyloxyethyl ester, 1-ethoxycarbonyloxyethyl ester, 1-isopropoxycarbonyloxyethyl ester, etc), phthalidylidene(lower)alkyl ester, or (5-lower alkyl-2-oxo-1,3-dioxol-4-yl)(lower)alkyl ester [e.g. (5-methyl-2-oxo-1,3-dioxol-4-yl) methyl ester, (5-ethyl-2-oxo-1,3-dioxol-4-yl)methyl ester, (5-propyl-2-oxo-1,3-dioxol-4-yl)ethyl ester, etc.]; lower alkenyl ester (e.g. vinyl ester, allyl ester, ect.); lower alkynyl ester (e.g. ethynyl ester, propynyl ester, etc.); ar(lower)alkyl ester which may have at least one suitable substituent(s) (e.g. benzyl ester, 4-methoxybenzyl ester, 4-nitrobenzyl ester, phenethyl ester, trityl ester, benzhydryl ester, bis(methoxyphenyl)methyl ester, 3,4-dimethoxybenzyl ester, 4-hydroxy-3,5-di-tert-butylbenzyl ester, etc.); aryl ester which may have at least one suitable substituent(s) (e.g. phenyl ester, 4-chlorophenyl ester, tolyl ester, tert-butylphenyl ester, xylyl ester, mesityl ester, cumenyl ester, etc.); phthalidyl ester; and the like.

Preferable examples of the esterified carboxy as mentioned above may include lower alkoxycarbonyl (e.g. methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, tert-pentyloxycarbonyl, hexloxycarbonyl, 1-cyclopropylethoxycarbonyl, etc.), and phenyl(lower)alkoxycarbonyl (e.g. benzyloxycarbonyl, benzhydryloxycarbonyl, etc.) which may have a nitro group.

Suitable "lower alkyl" may include straight or branched one, having 1 to 6 carbon atom(s), such as methyl, ethyl, propyl, isopropyl, butyl, t-butyl, pentyl, hexyl or the like.

Suitable "halogen" may include chlorine, bromine, fluorine and iodine.

Suitable "acid residue may include acyloxy, azido, halogen and the like, wherein acyl moiety in the term "acyloxy" and halogen can be referred to the ones as exemplified above.

Suitable "acylamino" and "protected amino" moieties in the terms "acylamino having protected amino"

and "acylamino having amino" can be referred to the ones as exemplified above.

The processes for preparing the object compounds of the present invention are explained in detail in the following.

PROCESS 1

The object compound (Ib) or a salt thereof can be prepared by reacting the compound (Ia) or its reactive derivative at the amino group or a salt thereof with an acylating agent.

Suitable reactive derivative at the amino group of the compound (Ia) may include Schiff's base type imino or its tautomeric enamine type isomer formed by the reaction of the compound (Ia) with a carbonyl compound such as aldehyde, ketone or the like; a silyl derivative formed by the reaction of the compound (Ia) with a silyl compound such as bis-(trimethylsilyl)acetamide, mono(trimethylsilyl)-acetamide or the like; a derivative formed by reaction of the compound (Ia) with phosphorus trichloride or phosgene, and the like.

Suitable acylating agent may include conventional one and can be shown by the formula: $R^4$—OH (XIV) (wherein $R^4$ is acyl) or its reactive derivative or a salt thereof.

Suitable salt of the compounds (Ia) and (XIV) may include an acid addition salt such as an organic acid salt (e.g. acetate, maleate, tartrate, methanesulfonate, benzenesulfonate, toluenesulfonate, etc.) or an inorganic acid salt (e.g. hydrochloride, hydrobromide, sulfate, phosphate, etc.); a metal salt (e.g. sodium salt, potassium salt, calcium salt, magnesium salt, etc.); ammonium salt; an organic amine salt (e.g. triethylamine salt, dicyclohexylamine salt, etc.), and the like.

Suitable reactive derivative of the compound (XIV) may include an acid halide, an acid anhydride, an activated amide, an activated ester, and the like. The suitable example may be an acid chloride, an acid azide; a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid etc.), dialkylphosphorous acid, sulforous acid, thiosulfuric acid, sulfuric acid, alkylcarbonic acid, aliphatic carboxylic acid (e.g. pivalic acid, pentanoic acid, isopentanoic acid, 2-ethylbutyric acid or trichloroacetic acid, etc.) or aromatic carboxylic acid (e.g. benzoic acid, etc.); a symmetrical acid anhydride; an activated amide with imidazole, 4-substituted imidazole, dimethylpyrazole, triazole or tetrazole; or an activated ester (e.g. cyanomethyl ester, methoxymethyl ester, dimethyliminomethyl [$(CH_3)_2N^+$=CH—] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.), or an ester with a N-hydroxy compound (e.g. N,N-dimethylhydroxylamine, 1-hydroxy-2-(1H)-pyridone, N-hydroxysuccinimide, N-hydroxyphthalimide, 1-hydroxy-6-chloro-1H-benzotriazole, etc.), and the like. These reactive derivatives can optionally be selected from them according to the kind of the compound (XIV) to be used.

The reaction is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

When the compound (XIV) is used in free acid form or its salt form in the reaction, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N-carbonylbis-(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; thionyl chloride; oxalyl chloride; triphenylphosphine; 2-ethyl-7-hydroxybenzisoxazolium salt; 2-ethyl-5-(m-sulfophenyl)isoxazolium hydroxide intra-molecular salt; 1-(p-chlorobenzenesulfonyloxy)-6-chloro-1H-benzotriazole; so-called Vilsmeier reagent prepared by the reaction of dimethylformamide with thionyl chloride, phosgene, phosphorus oxychloride, etc.; or the like.

The reaction may also be carried out in the presence of an inorganic or organic base such as an alkali metal bicarbonate, tri(lower)alkylamine, pyridine, N-(lower)alkylmorphorine, N,N-di(lower)-alkylbenzylamine, or the like. The reaction temperature is not critical, and the reaction is usually carried out under cooling or at ambient temperature.

In the present reaction, a syn isomer of the object compound (Ib) can be obtained preferably by conducting the present reaction of the compound (Ia) with the corresponding syn isomer of the starting compound (XIV).

PROCESS 2

The object compound (I) or a salt thereof can be prepared by subjecting the compound (II) or a salt thereof to elimination reaction of the carboxy protective group.

Suitable salt of the compound (II) can be referred to the acid addition salt exemplified for the compound (Ia).

In the present elimination reaction, all conventional methods used in the elimination reaction of the carboxy protective group, for example, hydrolysis, reduction, elimination using Lewis acid, etc. are applicable. When the carboxy protective group is an ester, it can be eliminated by hydrolysis or elimination using Lewis acid. The hydrolysis is preferably carried out in the presence of a base or an acid. Suitable base may include an inorganic base and an organic base as aforementioned.

Suitable acid may include an organic acid (e.g. formic acid, acetic acid, propionic acid, etc.) and an inorganic acid (e.g. hydrochloric acid, hydrobromic acid, sulfuric acid, etc.).

The present hydrolysis is usually carried out in an organic solvent, water or a mixed solvent thereof.

The reaction temperature is not critical, and it may suitably be selected in accordance with the kind of the carboxy protective group and the elimination method.

The elimination using Lewis acid is preferable to eliminate substituted or unsubstituted ar(lower)-alkyl ester and carried out by reacting the compound (II) or a salt thereof with Lewis acid such as boron trihalide (e.g. boron trichloride, boron trifluoride, etc.), titanium tetrahalide (e.g. titanium tetrachloride, titanium tetrabromide, etc.), tin tetrahalide (e.g. tin tetrachloride, tin tetrabromide etc.), aluminum halide (e.g. aluminum chloride, aluminum bromide, etc.), trihaloacetic acid (e.g. trichloroacetic acid, trifluoroacetic acid, etc.) or the like. This elimination reaction is preferably carried out in the presence of cation trapping agents (e.g. anisole, phenol, etc.) and is usually carried out in a solvent such as nitroalkane (e.g. nitromethane, nitroethane, etc.), alkylene halide (e.g. methylene chloride, ethylene chloride, etc.), diethyl ether, carbon disulfide or any other solvent which does not adversely affect the reaction. These solvents may be used as a mixture thereof.

The reductive elimination can be applied preferably for elimination of the protective group such as halo(lower)alkyl (e.g. 2-iodoethyl, 2,2,2-trichloroethyl, etc.) ester, ar(lower)alkyl (e.g. benzyl, etc.) ester or the like. The reduction method applicable for the elimination reaction may include, for example, reduction by using a conbination of a metal (e.g. zinc, zinc amalgam, etc.) or a salt of chromium compound (e.g. chromous chloride, chromous acetate, etc.) and an organic or an inorganic acid (e.g. acetic acid, propionic acid, hydrochloric acid, etc.); and conventional catalytic reduction in the presence of a conventional metallic catalyst (e.g. palladium carbon, Raney nickel, etc.).

The reaction temperature is not critical, and the reaction is usually carried out under cooling, at ambient temperature or under warming.

The present elimination reaction of the carboxy protective group includes, within its scope, the cases that another protected carboxy and/or protected amino group(s) are converted into the corresponding free carboxy and/or amino group(s) during the reaction or the post-treating step of the present process.

PROCESS 3

The object compound (I) or a salt thereof can be prepared by reacting the compound (III) or a salt thereof with a lower alkylating agent.

Suitable salt of the compound (I) or (III) can be referred to the ones as exemplified for the compound (Ia).

The lower alkylating agent to be used in the present alkylation reaction may include conventional one such as mono(or di)lower alkyl sulfate (e.g. dimethyl sulfate, etc.), lower alkyl lower alkanesulfonate (e.g. methyl methanesulfonate, etc.), halo(lower)alkane (e.g. bromomethane, iodomethane, iodoethane, etc.), or the like.

When lower alkyl ester of an acid is used as a lower alkylating agent, the reaction is usually carried out in a solvent such as water, acetone, tetrahydrofuran, ethanol, ether, dimethylformamide or any other solvent which does not adversely influence the reaction.

The present reaction is preferably carried out in the presence of a base such as an inorganic base or an organic base as aforementioned.

The reaction temperature is not critical and the reaction is usually carried out under cooling to heating around boiling point of the solvent.

PROCESS 4

The object compound (Ia) or a salt thereof can be prepared by subjecting the compound (Ib) or a salt thereof to deacylation reaction.

The present deacylation reaction is carried out in accordance with a conventional method such as hydrolysis; reduction; deacylation using Lewis acid; deacylation method by reacting the compound (Ib) with iminohalogenating agent and then with iminoetherifying agent; and, if necessary, subjecting the resulting compound to hydrolysis; or the like.

Among these methods, "the deacylation method by reacting the compound (Ib) with iminohalogenating agent and then with iminoetherifying agent, and, if necessary, subjecting the resulting compound to hydrolysis" is preferable method.

Suitable iminohalogenating agent may include phosphorus halide (e.g. phosphorus trichloride, phosphorus pentachloride, phosphorus tribromide, phosphorus pentabromide, etc.), phosphorus oxychloride, thionyl chloride, phosgene and the like. The reaction temperature is not critical, and the reaction is usually carried out under cooling or at ambient temperature.

In case that the compound (Ib) has a free carboxy group at the 4-position, this reaction is preferably carried out by protecting the free carboxy group with a sililating agent (e.g. trimethylsilyl chloride, trimethylsilylacetamide, bis(trimethylsilyl)acetamide, etc.) before this reaction.

Suitable iminoetherifying agent reacted with thus obtained reaction product may include an alcohol, metal alkoxide and the like. Suitable alcohol may include alkanol (e.g. methanol, ethanol, propanol, isopropanol, butanol, t-butanol, 1,3-butanediol, etc.) which may be substituted with alkoxy (e.g. methoxy, ethoxy, propoxy, isopropoxy, butoxy, etc.). Suitable metal alkoxide may include alkali metal alkoxide (e.g. sodium alkoxide, potassium alkoxide, etc.), alkaline earth metal alkoxide (e.g. calcium alkoxide, barium alkoxide, etc.) and the like. The reaction temperature is not critical, and the reaction is usually carried out under cooling or at ambient temperature.

Thus obtained product is, if necessary, subjected to hydrolysis. The hydrolysis can readily be carried out by pouring the reaction mixture obtained above into water, but there may be previously added a hydrophilic solvent (e.g. methanol, ethanol, etc.), a base (e.g. alkali metal bicarbonate, trialkylamine, etc.) or an acid (e.g. diluted hydrochloric acid, acetic acid, etc.) to the water.

The reaction temperature is not critical and may be suitably selected in accordance with the kind of the protective group of the amino group and the elimination method as mentioned above, and the present reaction is preferably carried out under a mild condition such as under cooling, at ambient temperature or slightly elevated temperature.

The present invention includes, within its scope, the case that the protected carboxy is transformed into the free carboxy group according to reaction conditions and kinds of the protective groups in the course of the reaction or in posttreatment. The hydrolysis may include a method using an acid or a base and the like. These methods may be selected depending on the kind of the acyl groups to be eliminated.

Suitable acid may include an organic or an inorganic acid, for example, formic acid, trifluoroacetic acid, benzenesulfonic acid, p-toluenesulfonic acid, hydrochloric acid and the like. The acid suitable for the reaction can be selected according to the kind of acyl group to be eliminated. When the deacylation reaction is conducted with the acid, it can be carried out in the presence or absence of a solvent. Suitable solvent may include an organic solvent, water or a mixed solvent thereof. When trifluoroacetic acid is used, the deacylation reaction may be preferably carried out in the presence of anisole.

Suitable base may include, for example, an inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), alkali metal acetate (e.g. sodium acetate, potassium acetate, etc.), alkaline earth metal phosphate (e.g. magnesium phosphate, calcium phosphate, etc.), alkali metal hydrogen phosphate (e.g. disodium hydrogen phosphate, dipotassium hydrogen phosphate, etc.), or the like, and an organic base such as trialkylamine (e.g. trimethylamine, triethylamine, etc.), picoline, N-methylpyrrolidine, N-methylmorpholine, 1,5-diazabicyclo[4,3,0]non-5-ene, 1,4-diazabicyclo[2,2,-2]octane, 1,5-diazabicyclo[5,4,0]undecene-5 or the like. The hydrolysis using a base is often carried out in water or a hydrophilic organic solvent or a mixed solvent thereof.

The reduction may include, for example, reduction with an alkali metal borohydride (e.g. sodium borohydride, etc.) catalytic reduction and the like.

The reaction temperature is not critical, and the reaction is usually carried out under cooling to warming.

The present invention includes, within its scope, the cases that the one type of tautomeric isomer is convented into the other type of isomer during the reaction and/or the post-treating step of the each process.

PROCESS 5

The object compound (Id) or a salt thereof can be prepared by subjecting the compound (Ic) or a salt thereof to elimination reaction of amino protective group.

The present elimination reaction can be carried out according to a similar manner to that of Process 4.

The object compound (I) may be transformed into its pharmaceutically acceptable salt as aforementioned by a conventional method.

The processes for preparing the starting compounds of the present invention are explained in detail in the following.

PROCESS A (i): (IV)→(V)

The compound (V) or its reactive derivative at the amino group or a salt thereof can be prepared by reacting the compound (IV) or its reactive derivative at the amino group or a salt thereof with triphenylphosphine.

The present reaction can be carried out in a solvent such as water, phosphate buffer, acetone, chloroform, acetonitrile, nitrobenzene, methylene chloride, ethylene chloride, formamide, dimethylformamide, methanol, ethanol, ether, tetrahydrofuran, dimethylsulfoxide, or any other organic solvent which does not adversely affect the reaction, preferably in ones having strong polarities. Among the solvents, hydrophilic solvents may be used in a mixture with water. The present reaction is preferably carried out in the presence of alkali metal halide (e.g. sodium iodide, potassium iodide, etc.), alkali metal thiocyanate (e.g. sodium thiocyanate, potassium thiocyanate, etc.) etc. The reaction temperature is not critical, and the reaction is usually carried out at ambient temperature, under warming or under heating.

(ii): (V)→(VI)

The compound (VI) or a salt thereof can be prepared by reacting the compound (V) or its reactive derivative at the amino group or a salt thereof with an acylating agent. The reaction can be carried out according to a similar manner to that of Process 1.

(iii): (VIa)+(VII)→(IIa)

The compound (IIa) or a salt thereof can be prepared by reacting the compound (VIa) or a salt thereof with the compound (VII) or a salt thereof.

The present invention is usually carried out in a solvent such as acetone, dioxane, acetonitrile, chloroform, methylene chloride, dimethylformamide, tetrahydrofuran, ethyl acetate or any other solvent which does not adversely affect the reaction. The reaction temperature is not critical and the reaction is usually carried out under cooling, at ambient temperature or under warming.

PROCESS B-(1)

(i): (IV)→(IVa)

The compound (IVa) or a salt thereof can be prepared by reacting the compound (IV) or its reactive derivative at the amino group or a salt thereof with an acylating agent.

The present reaction can be carried out in a similar manner to that of aforementioned Process 1.

(ii): (IVb)→(Va)

The compound (Va) or a salt thereof can be prepared by reacting the compound (IVb) or a salt thereof with triphenylphosphine.

The present reaction can be carried out according to a similar manner to that of aforementioned Process A-(i).

(iii): (VIII)→(Va)

The compound (Va) or a salt thereof can be prepared by reacting the compound (VIII) or its reactive derivative at the hydroxymethyl group or a salt thereof with triphenylphosphine.

The present reaction can be carried out according to a similar manner to that of aforementioned Process A-(i).

(iv): (Va)+(IX)→(IIIa)

The compound (IIIa) or a salt thereof can be prepared by reacting the compound (Va) or a salt thereof with the compound (IX) or a salt thereof.

The present reaction is usually carried out in a solvent such as water, acetone, dioxane, acetonitrile, chloroform, methylene chloride, tetrahydrofuran, dimethylformamide, ethyl acetate or any other solvent which does not adversely affect the reaction.

The reaction is preferably carried out in the presence of a base such as alkali metal hydroxide, alkali metal carbonate, alkali metal bicarbonate, trialkylamine, pyridine, or the like and preferably carried out around alkaline or neutral conditions. The reaction temperature is not critical and the reaction is usually carried out under cooling, at ambient temperature or under warming.

PROCESS B-(2)

(i): (VIII)→(IX)

The compound (IX) or a salt thereof can be prepared by oxidizing the compound (VIII) or its reactive derivative at the hydroxymethyl group or a salt thereof.

Suitable reactive derivative at the hydroxymethyl group of the compound (VIII) may include the compound wherein the hydroxymethyl group of the compound (VIII) is transformed into methyl group having an acid residue such as halogen (e.g. chlorine, bromine, etc.), arenesulfonyloxy (e.g. p-toluenesulfonyloxy, p-nitrobenzenesulfonyloxy, etc.), haloformyloxy (e.g. chloroformyloxy, etc.) or the like.

Suitable oxidizing agent to be used in this oxidation reaction may include conventional ones which can oxidize hydroxymethyl or its reactive derivatives at the hydroxymethyl group to formyl.

Said oxidizing agent may include (1) an activated dimethylsulfoxide formed by a reaction of dimethylsulfoxide and dicyclohexylcarbodiimide, dimethylsulfoxide and acetic anhydride, dimethylsulfoxide and phosphorus pentoxide, dimethylsulfoxide and sulfur trioxide-pyridine, dimethylsulfoxide and keteneimine, dimethylsulfoxide and chlorine, dimethylsulfoxide and mercuric acetate, dimethylsulfide and N-chlorosuccinimide, dimethylsulfide (or methylphenylsulfide) and chlorine, etc.; (2) chrome compound such as chromium trioxidepyridine, chromium trioxide-sulfuric acid, alkali metal dichromate (e.g. sodium dichromate, potassium dichromate, etc.), lower alkyl chromate (e.g. t-butyl chromate, etc.) and the like.

The oxidation using dimethylsulfoxide and dicyclohexylcarbodiimide is preferably carried out in the presence of proton-donor such as an acid (e.g. phosphoric acid, trifluoroacetic acid, dichloroacetic acid, etc.), a mixture of acid and base (e.g. trifluoroacetic acid-pyridine, phosphoric acid-pyridine, etc.) or the like.

The present oxidation reaction is carried out without or in the presence of an acid or a base and it is optionally selected according to a kind of oxidizing agent to be used.

The present oxidation is carried out without or with solvent such as benzene, toluene, chloroform, methylene chloride, carbon tetrachloride, diethyl ether, dimethylformamide or any other solvent which does not adversely affect the reaction, and the solvent is optionally selected according to a kind of oxidizing agent to be used.

In case that the starting compound of the present oxidation reaction is in a form of reactive derivatives at the hydroxymethyl group, suitable oxidizing agent may include dimethylsulfoxide and the like. The present oxidation is preferably carried out in the presence of a base (e.g. sodium bicarbonate, triethylamine, etc.).

The reaction temperature of the oxidation reaction of this process is not critical, and the reaction is carried out under cooling, at ambient temperature, under warming or under heating. The reaction temperature is optionally selected according to a kind of oxidizing agent to be used.

(ii): (IX)→(X)

The compound (X) or a salt thereof can be prepared by subjecting the compound (IX) or a salt thereof to isomerization reaction.

The present reaction is usually carried out in a solvent such as water, acetone, dioxane, acetonitrile, chloroform, methylene chloride, tetrahydrofuran, dimethylsulfoxide, ethyl acetate or any other solvent which does not adversely affect the reaction.

The reaction is preferably carried out in the presence of a base such as alkali metal hydroxide, alkali metal carbonate, alkali metal bicarbonate, trialkylamine, pyridine or the like.

The reaction temperature is not critical and the reaction is preferably carried out under cooling or at ambient temperature.

(iii): (X)+(XI)→(XII)

The compound (XII) or a salt thereof can be prepared by reacting the compound (X) or a salt thereof with the compound (XI) or a salt thereof. The present reaction can be carried out in a similar manner to that of aforementioned Process B-(1)-(iv).

(iv): (XII)→(XIII)

The compound (XIII) or a salt thereof can be prepared by oxidizing the compound (XII) or a salt thereof.

The present oxidation reaction can be carried out by a conventional method which is applied for the transformation of —S— into

for example by using an oxidizing agent such as m-chlorobenzoic acid, perbenzoic acid, peracetic acid, ozone, hydrogen peroxide, periodic acid or the like.

The present invention is usually carried out in a solvent such as water, acetone, dioxane, acetonitrile, chloroform, methylene chloride, tetrahydrofuran, ethyl acetate or any other solvent which does not adversely affect the reaction.

The reaction temperature is not critical and the reaction is preferably carried out under cooling or at ambient temperature.

(v): (XIII)→(IIIa)

The compound (IIIa) or a salt thereof can be prepared by reducing the compound (XIII) or a salt thereof.

The present reduction can be carried out by a conventional method which is applied for the transformation of

into —S—, for example, by using phosphorus trichloride, a combination of stannous chloride and acetyl chloride, a combination of an alkali metal iodide (e.g. sodium iodide, etc.) and trihaloacetic anhydride (e.g. trifluoroacetic anhydride, etc.), and the like.

The present reduction is usually carried out in a solvent such as acetone, dioxane, acetonitrile, dimethylformamide benzene, hexane, chloroform, methylene chloride, ethylene chloride, tetrahydrofuran, ethyl acetate, or any other solvent which does not adversely affect the reaction.

The reaction temperature is not critical and the reaction is usually carried out under cooling or at ambient temperature.

PROCESS B-(3)

(i): (IIIb)→(IIIc)

The compound (IIIc) or its reactive derivative at the amino group or a salt thereof can be prepared by subjecting the compound (IIIb) or a salt thereof to deacylation reaction.

The present reaction can be carried out in a similar manner to that of aforementioned Process 4.

(ii): (IIIc)→(IIIb)

The compound (IIIb) or a salt thereof can be prepared by reacting the compound (IIIc) or its reactive derivative at the amino group or a salt thereof with an acylating agent.

The present reaction can be carried out in a similar manner to that of aforementioned Process 1.

PROCESS B-(4)

(i): (IIId)→(III)

The compound (III) or a salt thereof can be prepared by subjecting the compound (IIId) or a salt thereof to elimination reaction of the carboxy protective group.

The present reaction can be carried out in a similar manner to that of aforementioned Process 2.

PROCESS B-(5)

The object compound (IIIf) or a salt thereof can be prepared by subjecting the compound (IIIe) or a salt thereof to elimination reaction of amino protective group.

Suitable salt of the compound (IIIe) can be referred to the salt, exemplified for the compound (I).

The elimination reaction is carried out in accordance with a conventional method such as hydrolysis; reduction; a method treating the compound (IIIe) wherein protected amino moiety is acylamino with iminohalogenating agent, iminoetherifying agent and then, if necessary, hydrolyzing the resultant; or the like. The hydrolysis may include a method using an acid or base or hydrazine and the like. These methods may be selected depending on the kind of the protective groups to be eliminated.

Among these methods, hydrolysis using an acid is one of the most common and preferable method for eliminating the protective groups such as substituted or unsubstituted alkoxycarbonyl, for example, tertpentyloxycarbonyl, lower alkanoyl (e.g. formyl, acetyl, etc.), cycloalkoxycarbonyl, substituted or unsubstituted aralkoxycarbonyl, aralkyl (e.g. trityl), substituted phenylthio, substituted aralkylidene, substituted alkylidene, substituted cycloalkylidene or the like. Suitable acid includes an organic or inorganic acid such as formic acid, trifluoroacetic acid, benzenesulfonic acid, p-toluenesulfonic acid, hydrochloric acid and the like, and the most suitable acid is an acid which can easily be removed from the reaction mixture by a conventional manner such as distillation under reduced pressure, for example, formic acid, trifluoroacetic acid, hydrochloric acid, etc. The acids can be selected according to the kind of the protective group to be eliminated. When the elimination reaction is conducted with an acid, it can be carried out in the presence or absence of a solvent.

Suitable solvent includes water, a conventional organic solvent or a mixture thereof.

The elimination reaction using trifluoroacetic acid may be carried out in the presence of anisole. The hydrolysis using hydrazine is commonly applied for eliminating a phthaloyl, succinyl type aminoprotective group.

The elimination using base is used for eliminating an acyl group such as trifluoroacetyl. Suitable base may include an inorganic base and an organic base.

The reductive elimination is generally applied for eliminating the protective group, for example, haloalkoxycarbonyl (e.g. trichloroethoxycarbonyl, etc.), substituted or unsubstituted aralkoxycarbonyl (e.g. benzyloxycarbonyl, etc.), 2-pyridylmethoxycarbonyl, etc. Suitable reduction may include, for example, reduction with an alkali metal borohydride (e.g. sodium borohydride, etc.), reduction with a combination of a metal (e.g. tin, zinc, iron, etc.) or the said metal together with a metal salt compound (e.g. chromous chloride, chromous acetate, etc.) and an organic or inorganic acid (e.g. acetic acid, propionic acid, hydrochloric acid, etc.); and catalytic reduction. Suitable catalyst includes a conventional one, for example. Raney nickel, platinum oxide, palladium carbon and the like.

Among the protective groups, the acyl group can generally be eliminated by hydrolysis. Especially, halogen substituted-alkoxycarbonyl and 8-quinolyloxycarbonyl groups are usually eliminated by treating with a heavy metal such as copper, zinc, or the like.

Among the protective groups, the acyl group can also be eliminated by treating with an iminohalogenating agent (e.g. phosphorus oxychloride, etc.) and an iminoetherifying agent such as lower alkanol (e.g. methanol, ethanol, etc.), if necessary, followed by hydrolysis.

The reaction temperature is not critical and may suitably be selected in accordance with the kind of the amino protective group and the elimination method as mentioned above, and the reaction is preferably carried out under a mild condition such as under cooling or at slightly elevated temperature.

The present invention includes, within its scope, the cases that another protected amino and/or protected carboxy group(s) are converted into the corresponding free amino and/or the free carboxy group(s) during the reaction or the post-treating step of the present process.

The object compounds (I) and pharmaceutically acceptable salts thereof of the present invention are novel compounds which exhibit high antibacterial activity and inhibit the growth of a wide variety of pathogenic microorganisms including Gram-positive and Gram-negative bacteria and are useful as antimicrobial agents. For therapeutic purpose, the compounds according to the present invention can be used in the form of conventional pharmaceutical preparation which contain said compounds, as an active ingredient, in admixture with a pharmaceutically acceptable carrier such as an organic or an inorganic solid or liquid excipient suitable for oral, parenteral or external administration. The pharmaceutical preparations may be in solid form such as capsule, tablet, dragee, ointment or suppository, or in liquid form such as solution, suspension, or emulsion. If desired, there may be included in the above preparations auxiliary substances, stabilizing agents, wetting or emulsifying agents, buffers and other commonly used additives.

While the dosage of the compounds will vary depending upon the age and condition of the patient, an average single dose of about 10 mg., 50 mg., 100 mg., 250 mg., 500 mg., and 1000 mg. of the compounds according to the present invention was proved to be effective for treating infectious diseases caused by pathogenic bacteria. In general, amounts between 1 mg/body and about 6,000 mg/body or even more may be administered per day.

In order to illustrate the usefulness of the object compound, anti-microbial activities of a representative compound of the present invention are shown below.

MINIMAL INHIBITORY CONCENTRATION

(A) Test Method

In vitro antibacterial activity was determined by the two-fold agar-plate dilution method as described below.

One loopful of an overnight culture of each test strain in Trypticase-soy broth ($10^8$ viable cells per ml) was streaked on heart infusion agar (HI-agar) containing graded concentrations of representative test compound, and the minimal inhibitory concentration (MIC) was expressed in terms of $\mu$g/ml after incubation at 37° C. for 20 hours.

(B) Test Compounds (1) 7-[2-(5-Amino-1,2,4-thiadiazol-3-yl)-2-ethoxyiminoacetamido]-3-[2-(1-methyl-3-pyridinio)vinyl]-3-cephem-4-carboxylate (syn isomer) (cis, trans mixture).

(2) 7-[2-(5-Amino-1,2,4-thiadiazol-3yl)-2-ethoxyiminoacetamido]-3-[2-(1-methyl-3-pyridinio)vinyl]-3-cephem-4-carboxylate (syn isomer) (trans isomer).

(C) Test Results

| Test strains | M.I.C. ($\mu$g/ml) | |
|---|---|---|
| | (1) | (2) |
| Escherichia coli 35 | <0.025 | <0.025 |
| Proteus vulgaris 2 | 0.050 | 0.050 |
| Citrobacter freundii 75 | 0.780 | 1.56 |
| Enterobacter cloacae 60 | 0.050 | 0.050 |

The following preparations and examples are given for the purpose of illustrating the present invention in more detail.

PREPARATION OF THE STARTING COMPOUNDS OF THE PRESENT INVENTION

PREPARATION 1

(1) Jones reagent (14.5 ml) was dropwise added to a suspension of benzhydryl 7-[2-(2-formamidothiazol-4-yl)-2-methoxyiminoacetamido]-3-hydroxymethyl-3-cephem-4-carboxylate (syn isomer) (19.5 g) in acetone (300 ml) at 0° to 3° C. under stirring and the mixture was stirred for 20 minutes at the same temperature. The reaction mixture was filtered and the filtrate was washed with acetone. To the mixture of the filtrate and washings was added ethyl acetate (300 ml) and washed with brine and dried over magnesium sulfate. The solution was evaporated and the residue was pulverized in diethyl ether to give benzhydryl 7-[2-(2-formamidothiazol-4-yl)-2-methoxyiminoacetamido]-3-formyl-3-cephem-4-carboxylate (syn isomer) (13.7 g).

IR (Nujol): 3250, 1780, 1720, 1670, 1600, 1540 cm$^{-1}$.

NMR $\delta$ (DMSO-d$_6$): 3.67 (2H, s), 3.95 (3H, s), 5.45 (1H, d, J=5 Hz), 6.15 (1H, dd, J=5,8 Hz), 7.30 (1H, s), 7.23-7.77 (11H, m), 8.57 (1H, s), 9.53 (1H, s), 9.83 (1H, d, J=8 Hz), 12.70 (1H, s).

(2) A solution of benzhydryl 7-[2-(2-formamidothiazol-4-yl)-2-methoxyiminoacetamido]-3-formyl-3-cephem-4-carboxylate (syn isomer) (3 g) and triethylamine (0.45 g) in tetrahydrofuran (30 ml) was stirred at ambient temperature for 40 minutes. To the reaction mixture was added ethyl acetate (50 ml) and washed with 3% hydrochloric acid and brine. The organic solution was dried over magnesium sulfate and evaporated. The residue was pulverized in diisopropyl ether to give benzhydryl 7-[2-(2-formamidothiazol-4-yl)-2-methoxyiminoacetamido]-3-formyl-2-cephem-4-carboxylate (syn isomer) (2.48 g).

IR (Nujol): 1780, 1730, 1665 cm$^{-1}$.

NMR $\delta$ (DMSO-d$_6$): 3.93 (3H, s), 5.3 (1H, d, J=4 Hz), 5.43 (1H, s), 5.73 (1H, d.d, J=4,8 Hz), 6.83 (1H, s), 7.13-7.72 (10H, m), 7.53 (1H, s), 8.3 (1H, s), 8.57 (1H, s), 9.40 (1H, s), 9.80 (1H, d, J=8 Hz), 12.63 (1H, broad s).

(3) To a solution of benzhydryl 7-[2-methoxyimino-2-(2-formamidothiazol-4-yl)acetamido]-3-formyl-2-cephem-4-carboxylate (syn isomer) (1.0 g) and 3-pyridazinylmethyl triphenyl phosphorium chloride (1.15 g) in methylene chloride (40 ml) and water (40 ml) was added tetra-n-butylammonium hydrogensulfate (25 mg). The solution was adjusted to pH 8.5 with 20% aqueous potassium carbonate and stirred at ambient temperature for 3 hours. The resultant solution was adjusted to pH 2.0 with 10% hydrochloric acid. The separated organic layer was washed with a saturated aqueous solution of sodium chloride, dried over magnesium sulfate and concentrated under reduced pressure. The residue was subjected to column chromatography on silica gel to give benzhydryl 7-[2-methoxyimino-2-(2-formamidothiazol-4-yl)acetamido]-3-[2-(3-pyridazinyl)vinyl]-2-cephem-4-carboxylate (syn isomer) (trans isomer) (0.2 g).

IR (Nujol): 3170, 1778, 1740, 1670, 1620 cm$^{-1}$.

NMR $\delta$ (DMSO-d$_6$): 3.90 (3H, s), 5.30 (1H, d, J=4 Hz), 5.67 (1H, dd, J=4 Hz, 8 Hz), 5.80 (1H, s), 6.83 (1H, s), 6.9-7.7 (16H, m), 8.47 (1H, s), 9.0 (1H, m), 9.68 (1H, d, J=8 Hz), 12.6 (1H, broad s).

(4) To a solution of benzhydryl 7-[2-methoxyimino-2-(2-formamidothiazol-4-yl)acetamido]-3-[2-(3-pyridazinyl)vinyl]-2-cephem-4-carboxylate (syn isomer) (trans isomer) (2.1 g) in methylene chloride (40 ml) was added a solution of 70% m-chloroperbenzoic acid (0.87 g) in methylene chloride (20 ml) at −35° C. with stirring. The reaction mixture was stirred at the same temperature for 20 minutes. The resultant solution was washed with 5% aqueous sodium bicarbonate. The separated organic layer was concentrated under reduced pressure and the residue was triturated in diisopropyl ether to give benzhydryl 7-[2-methoxyimino-2-(2-formamidothiazol-4-yl)acetamido]-3-[2-(3-pyridazinyl)vinyl]-3-cephem-4-carboxylate-1-oxide (syn isomer) (trans isomer) (1.85 g).

IR (Nujol): 3200, 1786, 1710, (sh), 1665 cm$^{-1}$.

NMR $\delta$ (DMSO-d$_6$): 3.91 (2H, m), 3.97 (3H, s), 5.17 (1H, d, J=5 Hz), 6.13 (1H, dd, J=5 Hz, 8 Hz), 7.12 (1H, s), 7.2-7.8 (14H, m), 8.10 (1H, d, J=16 Hz), 8.58 (1H, s), 9.17 (1H, m), 9.33 (1H, d, J=8 Hz), 12.4 (1H, broad s).

(5) To a solution of benzhydryl 7-[2-methoxyimino-2-(2-formamidothiazol-4-yl)acetamido]-3-[2-(3-pyridazinyl)vinyl]-3-cephem-4-carboxylate-1-oxide (syn isomer) (trans isomer) (1.8 g) in N,N-dimethylformamide (18 ml) was added phosphorus trichloride (0.45 ml) at −30° C. with stirring. The reaction mixture was stirred at −15° to −10° C. for 30 minutes and added dropwise to ice-water (100 ml). The suspension was adjusted to pH 7.5 with saturated aqueous sodium bicarbonate. The precipitate was collected by filtration, washed with water, dried under reduced pressure, and subjected to column chromatography on silica gel to give benzhydryl 7-[2-methoxyimino-2-(2-formamidothiazol-4-yl)-acetamido]-3-[2-(3-pyridazinyl)vinyl]-3-cephem-4-carboxylate (syn isomer) (trans isomer) (0.9 g).

IR (Nujol): 1780, 1710, 1671 cm$^{-1}$.

NMR δ (DMSO-d$_6$): 3.93 (3H, s), 4.0 (2H, m), 5.35 (1H, d, J=5 Hz), 6.02 (1H, dd, J=5 Hz, 8 Hz), 7.06 (1H, s), 7.2 (1H, d, J=16 Hz), 7.2–7.8 (13H, m), 7.88 (1H, d, J=16 Hz), 8.55 (1H, s), 9.13 (1H, m), 9.82 (1H, d, J=8 Hz), 12.6 (1H, broad s).

(6) To a solution of benzhydryl 7-[2-methoxyimino-2-(2-formamidothiazol-4-yl)acetamido]-3-[2-(3-pyridazinyl)vinyl]-3-cephem-4-carboxylate (syn isomer) (trans isomer) (0.85 g) in methanol (45 ml) and tetrahydrofuran (9 ml) was added conc.hydrochloric acid (0.56 ml) and the mixture was stirred at ambient temperature for 1.5 hours. The resultant solution was adjusted to pH 7.0 with 5% aqueous sodium bicarbonate and concentrated under reduced pressure. The residue was dissolved in ethyl acetate (150 ml). The organic layer was washed with a saturated aqueous solution of sodium chloride, dried over magnesium sulfate and evaporated in vacuo to give benzhydryl 7-[2-methoxyimino-2-(2-aminothiazol-4-yl)acetamido]-3-[2-(3-pyridazinyl)vinyl]-3-cephem-4-carboxylate (syn isomer) (trans isomer) (0.68 g).

IR (Nujol): 3300, 1770, 1713, 1662, 1607 cm$^{-1}$.

NMR δ (DMSO-d$_6$): 3.87 (3H, s), 3.9 (2H, m), 5.33 (1H, d, J=5 Hz), 5.93 (1H, dd, J=5 Hz, 8 Hz), 6.78 (1H, s), 7.03 (1H, s), 7.12 (1H, d, J=16 Hz), 7.1–7.8 (14H, m), 7.84 (1H, d, J=16 Hz), 9.10 (1H, m), 9.67 (1H, d, J=8 Hz).

(7) To a solution of benzhydryl 7-[2-methoxyimino-2-(2-aminothiazol-4-yl)acetamido]-3-[2-(3-pyridazinyl)-vinyl]-3-cephem-4-carboxylate (syn isomer) (trans isomer) (0.65 g) in methylene chloride (6.5 ml) and anisole (1.5 ml) was added trifluoroacetic acid (3.0 ml) under ice-cooling with stirring. The reaction mixture was stirred at ambient temperature for 30 minutes. The resultant solution was added dropwise to diisopropyl ether (100 ml), and the precipitate was collected by filtration, dissolved in an aqueous solution of sodium bicarbonate. The aqueous layer (100 ml) was washed with ethyl acetate (50 ml) twice, concentrated to 30 ml under reduced pressure and adjusted to pH 3.0 with 10% hydrochloric acid. The precipitate was collected by filtration, washed with water and dried over phosphorus pentoxide under reduced pressure to give 7-[2-methoxyimino-2-(2-aminothiazol-4-yl)acetamido]-3-[2-(3-pyridazinyl)vinyl]-3-cephem-4-carboxylic acid (syn isomer) (trans isomer) (0.37 g).

IR (Nujol): 3250, 1775, 1660, 1611 cm$^{-1}$.

NMR δ (DMSO-d$_6$): 3.87 (3H, s), 3.9 (2H, m), 5.28 (1H, d, J=5 Hz), 5.85 (1H, dd, J=5 Hz, 8 Hz), 6.77 (1H, s), 7.12 (1H, d, J=16 Hz), 7.67 (2H, m), 8.00 (1H, d, J=16 Hz), 9.07 (1H, m), 9.63 (1H, d, J=8 Hz).

PREPARATION 2

(1) Benzhydryl 7-phenylacetamido-3-formyl-2-cephem-4-carboxylate (5.1 g) was added to the mixture of 2-pyridyl methylene triphenylphosphonium chloride (4.7 g), water (25 ml) and dichloromethane (50 ml) and the solution was stirred at ambient temperature for 2 hours under keeping the pH 8.8 to 9.0 with 20% aqueous sodium carbonate.

The separated organic layer was washed with brine, and dried over magnesium sulfate and evaporated to give a crude product. The crude product was added to ethyl acetate (300 ml). The precipitate was filtered, washed with ethyl acetate and di-isopropyl ether, and dried to give benzhydryl 7-phenylacetamido-3-[2-(2-pyridyl)vinyl]-2-cephem-4-carboxylate (trans isomer) (2.8 g).

IR (Nujol): 3150, 1770, 1730, 1670, 1620, 1535 cm$^{-1}$.

NMR δ (DMSO-d$_6$): 3.60 (2H, s), 5.28 (1H, d, J=5 Hz), 5.50 (1H, dd, J=5 Hz, 8 Hz), 5.72 (1H, s), 7.02 (1H, d, J=17 Hz), 7.13–7.67 (16H, m), 7.90 (1H, d, J=17 Hz), 7.7–8.50 (3H, m), 8.72 (1H, d, J=4 Hz), 9.30 (1H, d, J=8 Hz).

(2) A solution of m-chloroperbenzoic acid (9.73 g) in dichloromethane (60 ml) was added dropwise to a solution of benzhydryl 7-phenylacetamido-3-[2-(2-pyridyl)-vinyl]-2-cephem-4-carboxylic acid (trans isomer) (27.6 g) in dichloromethane (280 ml) at −25° to −30° C. and the solution was stirred for 10 minutes at the same temperature. The reaction mixture was poured into water (100 ml). The separated organic layer was washed with 2% aqueous sodium bicarbonate and brine, dried over magnesium sulfate and evaporated to give benzhydryl 7-phenylacetamido-3-[2-(2-pyridyl)vinyl]-3-cephem-4-carboxylate-1-oxide (trans isomer) (24.5 g)

IR (Nujol): 3270, 1780, 1700, 1640, 1580, 1560, 1530 cm$^{-1}$.

NMR δ (DMSO-d$_6$): 3.67 (2H, s), 3.72 and 4.55 (2H, ABq, J=18 Hz), 5.05 (1H, d, J=5 Hz), 5.93 (1H, dd, J=5 Hz, 8 Hz), 7.02 (1H, s), 7.05 (1H, d, J=17 Hz), 8.12 (1H, d, J=17 Hz), 7.05–8.67 (19H, m).

(3) Phosphorus trichloride (15.2 g) was added to the solution of benzhydryl 7-phenylacetamido-3-[2-(2-pyridyl)vinyl]-3-cephem-4-carboxylate-1-oxide (trans isomer) (22.2 g) in dimethylformamide (220 ml) at −30° C. and the solution was stirred at −30° to −25° C. for 10 minutes. The reaction mixture was poured into cold water (1 l) and resulting precipitates were collected by filtration. The filtrate was dissolved in ethyl acetate (300 ml) and the ethyl acetate layer was washed with brine, dried over magnesium sulfate and evaporated to give benzhydryl 7-phenylacetamido-3-[2-(2-pyridyl)-vinyl]-3-cephem-4-carboxylate (trans isomer) (15.9 g).

IR (Nujol): 3300, 1770, 1695, 1645, 1575, 1555, 1520 cm$^{-1}$.

NMR δ (DMSO-d$_6$): 3.60 (2H, s), 3.95 (2H, ABq, J=18 Hz), 5.27 (1H, d, J=5 Hz), 5.83 (1H, dd, J=5 Hz, 8 Hz), 7.07 (1H, s), 7.15 (1H, d, J=17 Hz), 7.92 (1H, d, J=17 Hz), 7.17–8.0 (18H, m), 8.60 (1H, d, J=5 Hz), 9.20 (1H, d, J=8 Hz).

(4) To a suspension of pyridine-phosphorus pentachloride complex prepared from pyridine (48 g) and phosphorus pentachloride (12.7 g) in methylene chloride (120 ml) was added benzhydryl 7-phenylacetamido-3-[2-(2-pyridyl)vinyl]-3-cephem-4-carboxylate (trans isomer) (12 g) under ice-cooling with stirring. The mixture was stirred at the same temperature for 30 minutes and poured into methanol (90 ml) at −25° C. The mixed solution was further stirred at −5° to −15° C. for 10 minutes and then was evaporated under reduced pressure. To the residue was added a mixture of tetrahydrofuran (200 ml), ethyl acetate (200 ml) and water (200 ml) and the mixture was adjusted to pH 6.5 with a saturated aqueous solution of sodium bicarbonate. The separated organic layer was washed with brine, dried over magnesium sulfate and evaporated to give benzhydryl 7-amino-3-[2-(2-pyridyl)-vinyl]-3-cephem-4-carboxylate (trans isomer) (6.6 g).

IR (Nujol): 3300, 1770, 1720, 1615, 1580 cm$^{-1}$.

NMR δ (DMSO-$d_6$): 3.93 (2H, ABq, J=18 Hz), 4.92 (1H, d, J=5 Hz), 5.20 (1H, d, J=5 Hz), 7.05 (1H, s), 7.15 (1H, d, J=17 Hz), 7.92 (1H, d, J=17 Hz), 7.17–8.10 (15H, m), 8.50–8.75 (1H, m).

(5) Vilsmeier reagent was prepared from phosphorus oxychloride (1.29 g) and dimethylformamido (0.62 g) in ethyl acetate (30 ml) in a usual manner. 2-(2-Formamidothiazol-4-yl)-2-methoxyiminoacetic acid (syn isomer) (1.6 g) was added to the stirred suspension of the Vilsmeier reagent in ethyl acetate (2 ml) and tetrahydrofuran (10 ml) under ice-cooling and stirred at the same temperature for 0.5 hours to produce an activated acid solution. N-(Trimethylsilyl)acetamide (5.0 g) was added to the stirred suspension of benzhydryl 7-amino-3-[2-(2-pyridyl)vinyl]-3-cephem-4-carboxylate (trans isomer) (3 g) in ethyl acetate (30 ml) and stirred at 40° to 43° C. for 30 minutes. To the clear solution was added the activated acid solution prepared above at −20° C. and stirred at the same temperature for 30 minutes. Water (30 ml) was added to the resulting solution, and separated organic layer was washed with 5% aqueous sodium bicarbonate and brine, dried over magnesium sulfate and evaporated to give benzhydryl 7-[2-methoxyimino-2-(2-formamidothiazol-4-yl)acetamido]-3-[2-(2-pyridyl)vinyl]-3-cephem-4-carboxylate (syn isomer) (trans isomer) (4.1 g).

IR (Nujol): 3150, 1770, 1710, 1670, 1610, 1540 cm$^{-1}$.

NMR δ (DMSO-$d_6$): 3.58 (2H, m), 3.92 (3H, s), 5.38 (1H, d, J=5 Hz), 6.0 (1H, dd, J=5 Hz, 8 Hz), 7.07 (1H, s), 7.13–8.28 (14H, m), 8.55 (1H, s), 8.50–8.77 (1H, m), 9.82 (1H, d, J=8 Hz).

(6) A mixture of benzhydryl 7-amino-3-[2-(2-pyriyl)vinyl]-3-cephem-4-carboxylate (trans isomer) (25 g) and N-(trimethylsilyl)acetamide (4.2 g) in ethyl acetate (20 ml) and tetrahydrofuran (10 ml) was stirred at ambient temperature for 20 minutes to give a clear solution. To the solution was added 2-ethoxyimino-2-(5-amino-1,2,4-thiadiazol-3-yl)-acetylchloride (syn isomer) (1.4 g) at −5° ~ −20° C. and stirred at the same temperature for 30 minutes. Water (20 ml) was added to the resulting solution, and the separated organic layer was washed with 5% aqueous sodium bicarbonate and brine, dried over magnesium sulfate and evaporated to give benzhydryl 7-[2-ethoxyimino-2-(5-amino-1,2,4-thiadiazol-3-yl)acetamido]-3-[2-(2-pyridyl)vinyl]-3-cephem-4-carboxylate (syn isomer) (trans isomer) (3.6 g).

IR (Nujol): 3250, 1775, 1710, 1670, 1610, 1520 cm$^{-1}$.

NMR δ (DMSO-$d_6$): 1.23 (3H, t, J=7 Hz), 3.83 (2H, m), 4.15 (2H, q, J=7 Hz), 5.28 (1H, d, J=5 Hz), 5.92 (1H, dd, J=5 Hz, 8 Hz), 6.98 (1H, s), 7.08 (1H, d, J=17 Hz), 7.60 (1H, d, J=17 Hz), 7.10–8.33 (13H, m), 8.55 (1H, d, J=5 Hz), 9.58 (1H, d, J=8 Hz).

PREPARATION 3

(1) The following compounds were obtained according to a similar manner to that of Preparation 2-(1)

(1) Benzhydryl 7-phenylacetamido-3-[2-(4-pyridyl)-vinyl]-2-cephem-4-carboxylate (trans isomer).

IR (Nujol): 3770, 1767, 1725, 1645 cm$^{-1}$.

NMR δ (DMSO-$d_6$): 3.57 (2H, s), 5.23 (1H, d, J=4 Hz), 5.50 (1H, dd, J=4 Hz, 8 Hz), 5.83 (1H, s), 6.85 (1H, s), 7.53 (1H, s), 6.6–7.8 (19H, m), 8.52 (2H, d, J=6 Hz), 9.16 (1H, d, J=8 Hz).

(2) Benzhydryl 7-phenylacetamido-3-[2-(3-pyridyl)-vinyl]-2-cephem-4-carboxylate (cis isomer).

IR (Nujol): 3250, 1760, 1720(s), 1650, 1520 cm$^{-1}$.

NMR δ (DMSO-$d_6$): 3.60 (2H, s), 5.20 (1H, d, J=5 Hz), 5.43 (1H, m), 5.80 (1H, s), 6.53 (2H, s), 6.80–8.50 (19H, m), 8.68 (2H, m), 9.27 (1H, d, J=8 Hz).

(2) The following compounds were obtained according to a similar manner to that of Preparation 2-(2).

(1) Benzhydryl 7-phenylacetamido-3-[2-(4-pyridyl)-vinyl]-3-cephem-4-carboxylate-1-oxide (trans isomer).

IR (Nujol): 1770, 1718, 1698, 1647 cm$^{-1}$.

NMR δ (DMSO-$d_6$): 3.66 (2H, s), 3.8 (2H, m), 5.07 (1H, d, J=4 Hz), 5.97 (1H, dd, J=4 Hz, 8 Hz), 6.9–8.2 (20H, m), 8.53 (2H, brs), 8.60 (1H, d, J=8 Hz).

(2) Benzhydryl 7-phenylacetamido-3-[2-(3-pyridyl)-vinyl]-3-cephem-4-carboxylate-1-oxide (cis isomer).

IR (Nujol): 3200, 1780, 1720, 1670 cm$^{-1}$.

NMR δ (DMSO-$d_6$): 3.50 (2H, m), 3.67 (2H, s), 5.03 (1H, d, J=5 Hz), 5.92 (1H, dd, J=5 Hz, 8 Hz), 6.52 (2H, s), 6.85 (1H, s), 7.08–8.0 (17H, m), 8.47 (3H, m).

(3) The following compounds were obtained according to a similar manner to that of Preparation 2-(3).

(1) Benzhydryl 7-phenylacetamido-3-[2-(4-pyridyl)-vinyl]-3-cephem-4-carboxylate (trans isomer).

IR (Nujol): 3270–3170, 1772, 1710, 1670 cm$^{-1}$.

NMR δ (DMSO-$d_6$): 3.60 (2H, s), 3.70, 4.13 (2H, ABq, J=17 Hz), 5.23 (1H, d, J=5 Hz), 5.82 (1H, dd, J=5 Hz, 8 Hz), 6.9–7.7 (20H, m), 8.50 (2H, br.s), 9.23 (1H, d, J=8 Hz).

(2) Benzhydryl 7-phenylacetamido-3-[2-(3-pyridyl)-vinyl]-3-cephem-4-carboxylate (cis isomer).

IR (Nujol): 3150, 1770, 1710, 1660, 1530 cm$^{-1}$.

NMR δ (DMSO-$d_6$): 3.47 (2H, ABq, J=18 Hz), 3.57 (2H, s), 5.27 (1H, d, J=5 Hz), 5.83 (1H, dd, J=5 Hz, 8 Hz), 6.52 (2H, s), 6.85 (1H, s), 7.17–8.0 (17H, m), 8.57 (1H, d, J=8 Hz).

(4) The following compounds were obtained according to a similar manner to that of Preparation 2-(4).

(1) Benzhydryl 7-amino-3-[2-(4-pyridyl)vinyl]-3-cephem-4-carboxylate (trans isomer).

IR (Nujol): 1770, 1719, 1583 cm$^{-1}$.

NMR δ (DMSO-$d_6$): 3.83 (2H, m), 4.87, 5.13 (2H, ABq, J=5 Hz), 6.9–7.6 (17H, m), 8.45 (2H, d, J=5 Hz).

(2) Benzhydryl 7-amino-3-[2-(3-pyridyl)vinyl]-3-cephem-4-carboxylate (cis isomer).

IR (Nujol): 3300, 1760, 1720 cm$^{-1}$.

NMR δ (DMSO-$d_6$): 3.42 (2H, ABq, J=18 Hz), 4.87 (1H, d, J=5 Hz), 5.12 (1H, d, J=5 Hz), 6.45 (2H, s), 6.77 (1H, s), 7.05–7.67 (12H, m), 8.38 (2H, m).

(3) Benzhydryl 7-amino-3-[2-(3-pyridyl)vinyl]-3-cephem-4-carboxylate (cis, trans mixture).

IR (Nujol): 3300, 1760, 1710 cm$^{-1}$.

NMR δ (DMSO-$d_6$): 3.87 (2H, m), 4.90 (1H, d, J=5 Hz), 5.15 (1H, d, J=5 Hz), 7.0–7.80 (15H, m), 8.43 (2H, m).

(5) The following compound was obtained according to a similar manner to that of Preparation 2-(5).

Benzhydryl 7-[2-(tert-butoxycarbonylmethoxyimino)-2-(2-formamidothiazol-4-yl)acetamido]-3-[2-(2-pyridyl)vinyl]-3-cephem-4-carboxylate (syn isomer) (trans isomer).

IR (Nujol): 3250, 1780, 1720, 1680, 1540 cm$^{-1}$.

NMR δ (DMSO-d$_6$): 1.43 (9H, s), 3.95 (2H, ABq, J=18 Hz), 4.67 (2H, s), 5.38 (1H, d, J=5 Hz), 6.0 (1H, dd, J=5 Hz, 8 Hz), 7.05 (1H, s), 7.18 (1H, d, J=17 Hz), 7.68 (1H, d, J=17 Hz), 7.19–8.15 (13H, m), 8.57 (1H, s), 8.50–8.75 (1H, m), 9.75 (1H, d, J=8 Hz).

(6) The following compounds were obtained according to a similar manner to that of Preparation 1-(6).

(1) Benzhydryl 7-[2-methoxyimino-2-(2-aminothiazol-4-yl)acetamido]-3-[2-(2-pyridyl)vinyl]-3-cephem-4-carboxylate (syn isomer) (trans isomer).

IR (Nujol): 3250, 1780, 1720, 1680, 1610, 1580, 1530 cm$^{-1}$.

NMR δ (DMSO-d$_6$): 3.63 (2H, m), 3.88 (3H, s), 5.30 (1H, d, J=5 Hz), 5.92 (1H, dd, J=5 Hz, 8 Hz), 6.97 (1H, d, J=17 Hz), 7.03 (1H, s), 7.97 (1H, d, J=17 Hz), 7.08–7.70 (14H, m), 8.45–8.67 (1H, m), 9.67 (1H, d, J=8 Hz).

(2) Benzhydryl 7-[2-(tert-butoxycarbonylmethoxyimino)-2-(2-aminothiazol-4-yl)acetamido]-3-[2-(2-pyridyl)vinyl]-3-cephem-4-carboxylate dihydrochlorate (syn isomer) (trans isomer).

IR (Nujol): 3200, 1780, 1720, 1680, 1610, 1570 cm$^{-1}$.

NMR δ (DMSO-d$_6$): 1.47 (9H, s), 3.93 (2H, broad s), 4.72 (2H, s), 5.42 (1H, d, J=5 Hz), 6.05 (1H, dd, J=5 Hz, 8 Hz), 7.05 (1H, s), 7.18 (1H, d, J=17 Hz), 7.80 (1H, J=17 Hz), 7.17–8.50 (13H, m), 8.72 (1H, d, J=5 Hz), 9.92 (1H, d, J=8 Hz).

(7) The following compounds were obtained according to a similar manner to that of Preparation 2-(6).

(1) Benzhydryl 7-[2-ethoxyimino-2-(5-amino-1,2,4-thiadiazol-3-yl)acetamido]-3-[2-(4-pyriyl)vinyl]-3-cephem-4-carboxylate (syn isomer) (trans isomer).

IR (Nujol): 3260, 1777, 1710, 1672, 1610 cm$^{-1}$.

NMR δ (DMSO-d$_6$): 1.20 (3H, t, J=7 Hz), 3.85 (2H, m), 4.15 (2H, q, J=7 Hz), 5.25 (1H, d, J=5 Hz), 5.92 (1H, dd, J=5 Hz, 8 Hz), 6.99 (1H, s), 6.9–7.8 (16H, m), 8.70 (2H, d, J=5 Hz), 9.60 (1H, d, J=8 Hz).

(2) Benzhydryl 7-[2-ethoxyimino-2-(5-amino-1,2,4-thiadiazol-3-yl)acetamido]-3-[2-(3-pyridyl)vinyl]-3-cephem-4-carboxylate (syn isomer) (cis isomer).

IR (Nujol): 3250, 1770, 1720, 1670, 1610, 1520 cm$^{-1}$.

NMR δ (DMSO-d$_6$): 1.10 (3H, t, J=7 Hz), 3.47 (2H, ABq, J=18 Hz), 4.22 (2H, q, J=7 Hz), 5.33 (1H, d, J=5 Hz), 5.97 (1H, dd, J=5 Hz, 8 Hz), 6.50 (2H, s), 6.83 (1H, s), 7.10–7.88 (12H, m), 8.40 (1H, m), 9.67 (1H, d, J=8 Hz).

(8) The following compounds were obtained according to a similar manner to that of Preparation 1-(7).

(1) 7-[2-methoxyimino-2-(2-aminothiazol-4-yl)acetamido]-3-[2-(2-pyridyl)vinyl]-3-cephem-4-carboxylic acid (syn isomer) (trans isomer)

IR (Nujol): 3300, 1770, 1670, 1625, 1570, 1520 cm$^{-1}$.

NMR δ (DMSO-d$_6$): 3.62 (2H, m), 3.88 (3H, s), 5.28 (1H, d, J=5 Hz), 4.83 (1H, dd, J=5 Hz, 8 Hz), 6.78 (1H, s), 7.05 (1H, d, J=17 Hz), 7.95 (1H, d, J=17 Hz), 7.0–8.18 (5H, m), 8.57 (1H, d, J=5 Hz), 9.65 (1H, d, J=8 Hz).

(2) 7-[2-ethoxyimino-2-(5-amino-1,2,4-thiadiazol-3-yl)acetamido]-3-[2-(2-pyridyl)vinyl]-3-cephem-4-carboxylic acid (syn isomer) (trans isomer).

IR (Nujol): 3250, 1770, 1670, 1620, 1575, 1520 cm$^{-1}$.

NMR δ (DMSO-d$_6$): 1.12 (3H, t, J=7 Hz), 3.90 (2H, ABq, J=18 Hz), 4.22 (2H, q, J=7 Hz), 5.27 (1H, d, J=5 Hz), 5.87 (1H, dd, J=5 Hz, 8 Hz), 7.03 (1H, d, J=17 Hz), 7.93 (1H, d, J=17 Hz), 7.17–8.38 (3H, m), 8.58 (1H, d, J=5 Hz), 9.62 (1H, d, J=8 Hz).

(3) 7-[2-ethoxyimino-2-(5-amino-1,2,4-thiadiazol-3-yl)acetamido]-3-[2-(4-pyridyl)vinyl]-3-cephem-4-carboxylic acid (syn isomer) (trans isomer).

IR (Nujol): 3200, 1770, 1665, 1630, 1608 cm$^{-1}$.

NMR δ (DMSO-d$_6$): 1.28 (3H, t, J=7 Hz), 3.93 (2H, m), 4.22 (2H, q, J=7 Hz), 5.28 (1H, d, J=5 Hz), 5.87 (1H, dd, J=5 Hz, 8 Hz), 7.07 (1H, d, J=16 Hz), 7.62 (2H, d, J=5 Hz), 7.73 (1H, d, J=16 Hz), 8.17 (2H, broad s), 8.65 (2H, d, J=5 Hz), 9.60 (1H, d, J=8 Hz).

(4) 7-[2-ethoxyimino-2-(5-amino-1,2,4-thiadiazol-3-yl)acetamido]-3-[2-(3-pyridyl)vinyl]-3-cephem-4-carboxylic acid (syn isomer) (cis isomer).

IR (Nujol): 3250, 1770, 1680, 1610, 1520 cm$^{-1}$.

NMR δ (DMSO-d$_6$): 1.18 (3H, t, J=7 Hz), 3.67 (2H, m), 4.17 (2H, q, J=7 Hz), 5.22 (1H, d, J=5 Hz), 5.82 (1H, dd, J=5 Hz, 8 Hz), 6.57 (2H, s), 7.10–7.88 (2H, m), 8.47 (2H, m), 9.58 (1H, d, J=8 Hz).

(5) 7-[2-carboxymethoxyimino-2-(2-aminothiazol)-4-yl)acetamido]-3-[2-(2-pyridyl)vinyl]-3-cephem-4-carboxylic acid (syn isomer) (trans isomer).

IR (Nujol): 3250, 1770, 1670, 1620, 1565, 1530 cm$^{-1}$.

NMR δ (DMSO-d$_6$): 3.93 (2H, ABq, J=18 Hz), 4.67 (2H, s), 5.33 (1H, d, J=5 Hz), 5.90 (1H, dd, J=5 Hz, 8 Hz), 6.87 (1H, s), 7.05 (1H, d, J=17 Hz), 8.0 (1H, d, J=17 Hz), 7.0–8.08 (3H, m), 8.62 (1H, d, J=5 Hz), 9.62 (1H, d, J=8 Hz).

PREPARATION 4

(1) Sodium iodide (1.8 g) was added to a solution of benzhydryl 7-amino-3-chloromethyl-3-cephem-4-carboxylate (5.0 g) and triphenylphosphine (3.2 g) in dimethyl formamide (15 ml) under ice-cooling and stirred for 3 hours at ambient temperature. The resulting solution was added dropwise to ethyl acetate (250 ml) under vigorous stirring. The precipitate, collected by filtration, was washed with ethyl acetate to give [4-benzhydryloxycarbonyl-7-amino-3-cephem-3-ylmethyl]triphenylphosphonium iodide hydrochloride (9.6 g).

IR (Nujol): 3330, 1780, 1700, 1645 cm$^{-1}$.

(2) (4-benzhydryloxycarbonyl-7-amino-3-cephem-3-ylmethyl)triphenylphosphonium iodide hydrochloride (5 g) was dissolved in a mixed solution of tetrahydrofuran (35 ml) and 35 ml of aqueous sodium bicarbonate (1.6 g). To the solution was added a solution of 2-(5-amino-1,2,4-thiadiazol-3-yl)-2-ethoxyimino acetylchloride hydrochloride (syn isomer) (2.6 g) in tetrahydrofuran at −3° C. to 3° C., and the solution was stirred for 30 minutes under keeping the pH 6.5 to 7.5 with 20% aqueous potassium carbonate. Ethyl acetate was added to the reaction mixture and the mixture was adjusted to pH 10.0 with 20% aqueous potassium carbonate. The separated organic layer was washed with saturated aqueous sodium chloride, dried over magnesium sulfate and evaporated to give benzhydryl 7-[2-(5-amino-1,2,4-thiadiazol-3-yl)-2-ethoxyiminoacetamido]-3-(triphenylphosphoranediylmethyl)-3-cephem-4-carboxylate (syn isomer) (4.5 g).

IR (Nujol): 1740, 1640 (br) cm$^{-1}$.

NMR δ (DMSO-d$_6$): 1.25 (3H, t, J=7.0 Hz), 3.11–3.77 (2H, m, over lap H$_2$O), 4.10 (2H, q, J=7.0 Hz), 5.19 (1H, d, J=4.0 Hz), 5.63 (1H, m), 6.70–8.27 (26H, m), 9.20 (1H, d, J=8.0 Hz).

(3) The following compounds were obtained according to a similar manner to that of Preparation 8-(2).

Benzhydryl 7-[2-(5-amino-1,2,4-thiadiazol-3-yl)-2-ethoxyiminoacetamido]-3-[2-(1-methyl-3-pyridinio)-vinyl]-3-cephem-4-carboxylate iodide (syn isomer) (cis trans mixture).

IR (Nujol): 1780, 1720, 1660, 1610 cm$^{-1}$.

NMR δ (DMSO-d$_6$): 1.27 (3H, t, J=7.0 Hz), 3.53 (2H, m), 4.20 (2H, q, J=7.0 Hz), 4.31 (2H, s), 5.37 (1H, d, J=4.0 Hz), 5.90 (1H, m), 6.58-8.30 (15H, m), 8.73 (1H, m), 9.54 (1H, d, J=8.0 Hz).

PREPARATION 5

(1) 2-(5-amino-1,2,4-thiadiazol-3-yl)-2-ethoxyiminoacetic acid (syn isomer) (14.4 g) was added to the stirred suspension of phosphorus pentachloride (13.8 g) in dichloromethane (150 ml) at −5° C. and stirred for 20 minutes at −10° C. to 0° C. Isopropyl ether was added to the reaction mixture at same temperature and stirred for 10 minutes at ambient temperature. The precipitate was filtered off and washed with isopropyl ether. N-(trimethylsilyl)acetamide (43.6 g) was added to the stirred suspension of benzhydryl 7-amino-3-chloromethyl-3-cephem-4-carboxylate hydrochloride (25 g) in ethyl acetate (250 ml). To the solution as obtained was added the above precipitate at −10° C. and stirred for 30 minutes at −10° C. to −5° C. Water was added to the reaction mixture. The separated organic layer was washed with a saturated aqueous sodium bicarbonate and water. The organic layer was dried over magnesium sulfate and evaporated to give benzhydryl 7-[2-(5-amino-1,2,4-thiadiazol-3-yl)-2-ethoxyiminoacetamido]-3-chloromethyl-3-cephem-4-carboxylate (syn isomer) (36.8 g).

IR (Nujol): 3270, 3140, 1775, 1720, 1670, 1620 cm$^{-1}$.

NMR δ (DMSO-d$_6$): 1.25 (3H, t, J=7.0 Hz), 3.61 (2H, m), 4.19 (2H, q, J=7.0 Hz), 4.43 (2H, s), 5.24 (1H, d, J=5.0 Hz), 5.95 (1H, d-d, J=5.0 Hz, 8.0 Hz), 6.95 (1H, s), 7.36 (10H, m), 8.12 (2H, broad s), 9.59 (1H, d, J=8.0 Hz).

(2) A mixture of benzhydryl 7-[2-(5-amino-1,2,4-thiadiazol-3-yl)-2-ethoxyiminoacetamido]-3-chloromethyl-3-cephem-4-carboxylate (syn isomer) (36.7 g) in ethyl acetate (600 ml), triphenyl phosphine (18.8 g) and sodium iodide (1 g) were boiled under reflux for 100 minutes. The precipitates were collected by filtration and washed with ethyl acetate to give [4-benzhydryloxycarbonyl-7-[2-(5-amino-1,2,4-thiadiazol-3-yl)-2-ethoxyiminoacetamido]-3-cephem-3-ylmethyl]-triphenylphosphonium chloride (syn iosmer) (31.1 g).

IR (Nujol): 1770, 1670, 1600 cm$^{-1}$.

NMR δ (DMSO-d$_6$): 1.23 (3H, t, J=7.0 Hz), 3.62 (2H, m), 4.19 (2H, q, J=7.0 Hz), 5.03-5.56 (2H, m), 5.38 (1H, d, J=5.0 Hz), 5.95 (1H, dd, J=5.0 Hz, 8.0 Hz), 6.30 (1H, s), 7.10-8.07 (25H, m), 8.36 (2H, broad s), 9.64 (1H, d, J=8.0 Hz).

(3) Nicotinaldehyde (1.1 g) was added to a solution of {4-benzhydryloxycarbonyl-7-[2-(5-amino-1,2,4-thiadiazol-3-yl)-2-ethoxyiminoacetamido]-3-cephem-3-ylmethyl}triphenylphosphonium chloride (syn isomer) (3.0 g) in tetrahydrofuran (30 ml) and water (15 ml) and the solution was adjusted to pH 9.0 with 20% aqueous sodium carbonate. The solution was stirred at ambient temperature for 2 hours under keeping the pH 8.8 to 9.2 with 20% aqueous potassium carbonate. Ethyl acetate and water were added to the resulting solution. The separated organic layer was washed with saturated aqueous sodium chloride and dried over magnesium sulfate. The crude product obtained by concentration was purified by silica gel column chromatography using a mixture of acetone and dichloromethane (rate 1:1) as eluent. The eluted fractions were evaporated to give benzhydryl 7-[2-(5-amino-1,2,4-thiadiazol-3-yl)-2-ethoxyiminoacetamido]-3-[2-(3-pyridyl)vinyl]-3-cephem-4-carboxylate (syn isomer) (cis-trans mixture) (1.1 g).

IR (Nujol): 1770, 1710, 1670, 1610 cm$^{-1}$.

NMR δ (DMSO-d$_6$): 1.26 and 1.30 (total 3H, each t, J=7.0 Hz), 3.48 (2H, q, J=18.0 Hz), 4.21 (2H, q, J=7.0 Hz), 5.33 (1H, d, J=5.0 Hz), 5.97 (1H, d-d, J=5.0 Hz, 8.0 Hz), 6.51 (1H, s), 6.83 (1H, s), 7.07-7.76 (13H, m), 8.17 (2H, s), 8.35-8.60 (2H, m), 9.74 (1H, d, J=8.0 Hz).

(4) Trifluoroacetic acid (1.2 ml) was added to a suspension of benzhydryl 7-[2-(5-amino-1,2,4-thiadiazol-3-yl)-2-ethoxyiminoacetamido]-3-[2-(3-pyridyl)vinyl]-3-cephem-4-carboxylate (syn isomer) (cis-trans mixture) (1.0 g) in dichloromethane (10 ml) and anisole (0.65 ml) at ambient temperature and stirred for 2 hours at the same temperature. To the resulting solution was added isopropyl ether (50 ml) and stirred. The precipitates, collected by filtration, were washed with diisopropyl ether. The precipitates were added to a mixture of ethyl acetate and water and adjusted to pH 7.5 with 20% aqueous potassium carbonate. The separated aqueous layer was adjusted to pH 3.5 with 10% hydrochloric acid under ice-cooling. The resulting precipitates were filtered off, washed with ice water and dried over phosphorus pentoxide in vacuo to give 7-[2-(5-amino-1,2,4-thiadiazol-3-yl)-2-ethoxyiminoacetamido]-3-[2-(3-pyridyl)vinyl]-3-cephem-4-carboxylic acid (syn isomer) (cis-trans mixture) (0.4 g).

IR (Nujol): 3240, 3140, 1765, 1665, 1610 cm$^{-1}$.

NMR δ (DMSO-d$_6$): 1.25 and 1.29 (total 3H, each t, J=7.0 Hz), 3.40 (2H, q, J=18.0 Hz), 4.18 and 4.22 (total 2H, each q, J=7.0 Hz), 5.26 (1H, d, J=5.0 Hz), 5.85 (1H, d-d, J=5.0 Hz, 8.0 Hz), 6.58 (1H, s), 7.04 (0.5H, d, J=17.0 Hz), 7.23-8.24 (3.5H, m), 8.28 (2H, broad s), 8.39-8.72 (2H, m), 9.58 (1H, d, J=8.0 Hz).

PREPARATION 6

(1) The following compound was obtained according to a similar manner to that of Preparation 5-(3).

Benzhydryl 7-[2-(2-formaminothiazol-4-yl)-2-methoxyiminoacetamido]-3-[2-(3-pyridyl)vinyl]-3-cephem-4-carboxylate (syn isomer) (cis-trans mixture).

IR (Nujol): 1765, 1670, 1640 cm$^{-1}$.

NMR δ (DMSO-d$_6$): 3.48 (2H, m), 3.91 (3H, s), 5.35 (1H, d, J=5.0 Hz), 5.98 (1H, d-d, J=5.0 Hz, 8.0 Hz), 6.52 (1H, s), 6.83 (1H, s), 6.85-7.71 (14H, m), 8.37-8.66 (3H, m), 9.80 (1H, d, J=8.0 Hz).

(2) The following compound was obtained according to a similar manner to that of Preparation 5-(4).

7-[2-(2-formamidothiazol-4-yl)-2-methoxyimino acetamido-3-[2-(3-pyridyl)vinyl]-3-cephem-4-carboxylic acid (syn isomer) (cis-trans mixture).

IR (Nujol): 1760, 1665 cm$^{-1}$.

NMR δ (DMSO-d$_6$): 3.43 (2H, q, J=18.0 Hz), 3.92 (3H, s), 5.29 (1H, d, J=5.0 Hz), 5.87 (1H, d-d, J=5.0 Hz, 8.0 Hz), 6.61 (1H, s), 6.85-8.31 (3H, m), 7.43 and 7.46 (Total 1H, each s), 8.38-8.77 (3H, m), 9.74 (1H, d, J=8.0 Hz).

(3) A mixture of 7-[2-(2-formamidothiazol-4-yl)-2-methoxyiminoacetamido]-3-[2-(3-pyridyl)vinyl]-3-cephem-4-carboxylic acid (syn isomer) (cis-trans mixture) (0.8 g) in methanol (6 ml), tetrahydrofuran (3 ml) and conc.hydrochloric acid (0.5 g) were stirred for 3 hours at ambient temperature. The resulting solution was added to a mixture of ethyl acetate and water and adjusted to pH 7.5 with 20% aqueous potassium carbonate. The separated aqueous layer was adjusted to pH 3.5 with 10% hydrochloric acid under ice-cooling. The precipitate was filtered off, washed with ice-water and dried over phosphorus pentoxide in vacuo to give 7-[2-(2-aminothiazol-4-yl)-2-methoxyiminoacetamido]-3-[2-(3-pyridyl)vinyl]-3-cephem-4-carboxylic acid (syn isomer) (cis-trans mixture) (0.3 g).

IR (Nujol): 3280, 1770, 1660, 1620 cm$^{-1}$.

NMR δ (DMSO-d$_6$): 3.39 (2H, q, J=18.0 Hz), 3.85 (3H, s), 5.23 (1H, d, J=5.0 Hz), 5.80 (1H, d-d, J=5.0 Hz, 8.0 Hz), 6.56 (1H, s), 6.77 (1H, s), 6.80–8.00 (3H, m), 8.35–8.68 (2H, m), 9.65 (1H, d, J=8.0 Hz).

PREPARATION 7

(1) A solution of phosphorus tribromide (5.0 g) in tetrahydrofuran (10 ml) was dropwise added to a mixture of benzhydryl 7-phenylacetamido-3-hydroxymethyl-3-cephem-4-carboxylate (25.7 g) in tetrahydrofuran (200 ml) at −10° to −5° C. and the mixture was stirred at the same temperature for 15 minutes. The resultant mixture was poured into a mixture of water (250 ml) and ethyl acetate (300 ml). The separated organic layer was washed with brine and dried over magnesium sulfate. The solvent was evaporated to give the oily product. The crude oily product was dissolved in ethyl acetate (250 ml) and triphenylphosphine (21 g) was added. The mixture was stirred at ambient temperature for 3 hours. The precipitate was collected by filtration and washed with ethyl acetate to give (4-benzhydryloxycarbonyl-7-phenylacetamido-3-cephem-3-ylmethyl)triphenyl phosphonium bromide (22.8 g).

IR (Nujol): 1780, 1710, 1665 cm$^{-1}$.

(2) Nicotinaldehyde (32.1 g) was added to a solution of [4-benzhydryloxycarbonyl-7-(2-phenylacetamido)-3-cephem-3-ylmethyl]triphenylphosphonium bromide (84.0 g) in a mixture of tetrahydrofuran (800 ml) and water (400 ml) and the solution was adjusted to pH 9.0 with 20% aqueous sodium carbonate. The solution was stirred at ambient temperature for 2 hours under keeping the pH 8.8 to 9.2 with 20% aqueous potassium carbonate. Ethyl acetate (800 ml) and water (800 ml) were added to the resulting solution. The separated organic layer was washed with saturated aqueous sodium chloride and dried over magnesium sulfate. The crude product obtained by concentration was purified by silica gel column chromatography using a mixture of acetone and dichloromethane (1:1 U/U) as eluent. The eluted fraction was evaporated to give benzhydryl 7-(2-phenylacetamido)-3-[2-(3-pyridyl)vinyl]-3-cephem-4-carboxylate (cis-trans mixture) (28.5 g).

IR (Nujol): 3250, 1770, 1710, 1660, 1530 cm$^{-1}$.

NMR δ (DMSO-d$_6$): 3.50 (2H, ABq, J=18 Hz), 3.58 (2H, s), 5.27 (1H, d, J=5 Hz), 5.80 (1H, dd, J=5 Hz, 8 Hz), 6.55 (1.5H, s), 6.82 (1H, s), 7.17–7.93 (17.5H, m), 8.50 (2H, d), 9.22 (1H, d, J=8 Hz).

(3) A mixture of benzhydryl 7-phenylacetamido-3-[2-(3-pyridyl)vinyl]-3-cephem-4-carboxylate (cis-trans mixture) (5.9 g), anisole (6 ml) and trifluoroacetic acid (20 ml) was stirred at ambient temperature for 30 minutes. The reaction mixture was added to di-iso-propylether (300 ml). The precipitate was collected by filtration, washed with di-iso-propylether to give 7-phenylacetamido-3-[2-(3-pyridyl)vinyl]-3-cephem-4-carboxylic acid trifluoroacetate (cis-trans mixture) (2.5 g).

IR (Nujol): 3200, 1760, 1660, 1520 cm$^{-1}$.

NMR δ (DMSO-d$_6$): 3.58 (2H, s), 3.45 (2H, ABq, J=18 Hz), 5.20 (1H, d, J=5 Hz), 5.70 (1H, dd, J=5 Hz, 8 Hz), 6.65 (1H, s), 7.17–8.33 (8H, m), 8.65 (2H, m), 9.15 (1H, d, J=8 Hz).

PREPARATION 8

(1) A solution of (4-benzhydryloxycarbonyl-7-phenylacetamido-3-cephem-3-ylmethyl)triphenyl phosphonium bromide (8.4 g) in tetrahydrofuran (50 ml) and water (50 ml) was adjusted to pH 11.0 with aqueous sodium hydroxide solution and the resultant solution was extracted with ethyl acetate and tetrahydrofuran. The organic layer was washed with brine and dried over magnesium sulfate. The solvent was evaporated and the residue was washed with ether to give benzhydryl 7-phenylacetamido-3-triphenylphosphoranediylmethyl)-3-cephem-4-carboxylate (4.5 g).

IR (Nujol): 3370, 1760, 1680, 1650 cm$^{-1}$.

(2) A solution of benzhydryl 7-phenylacetamido-3-(triphenylphosphoranediylmethyl)-3-cephem-4-carboxylate (3.8 g) and 1-methyl-3-formyl pyridinium iodide (3.74 g) in dimethylformamide (50 ml) was stirred at ambient temperature for 5 hours. The mixture was poured into a mixture of diethylether-ethyl acetate (2:1) and decanted. Water was added to the residue and the mixture was adjusted to pH 8.0 with 20% aqueous potassium carbonate. The solution was extracted with a mixture of ethyl acetate-tetrahydrofuran and the solution was dried over magnesium sulfate. The solvent was evaporated in vacuo and the residue was pulverized in diethyl ether to give benzhydryl 7-phenylacetamido-3-[2-(1-methyl-3-pyridinio)vinyl]-3-cephem-4-carboxylate iodide (cis-trans mixture) (2.1 g).

IR (Nujol): 1770, 1720, 1660 cm$^{-1}$.

NMR δ (DMSO-d$_6$): 3.6 (2H, s), 3.6 (2H, m), 4.33 (3H, s), 5.28 (1H, m), 5.78 (1H, m), 6.57–8.23 (19H, m), 8.6–9.4 (3H, m).

PREPARATION 9

The mixture of trans and cis isomer of benzhydryl 7-[2-(5-amino-1,2,4-thiadiazol-3-yl)-2-ethoxyiminoacetamido]-3-[2-(3-pyridyl)vinyl]-3-cephem-4-carboxylate (syn isomer) (8 g) was subjected to medium pressure column chromatography on silica gel [merck, kieselgel 60. (230–400 mesh, 160 g)] using chloroformacetic acid (rate 20:1 ~ 10:1) as eluent. The fraction containing cis form isomer was washed with saturated sodium bicarbonate solution and brine and dried over magnesium sulfate. The solution was evaporated and the residue was pulverized with diethyl ether to give cis form isomer of benzhydryl 7-[2-(5-amino-1,2,4-thiadiazol-3-yl)-2-ethoxyiminoacetamido]-3-[2-(3-pyridyl)vinyl]-3-cephem-4-carboxylate (syn isomer) (4.1 g). Then the second fraction containing trans form isomer was washed with saturated sodium bicarbonate solution and brine and dried over magnesium sulfate. The solution was evaporated and the residue was pulverized with diethyl ether to give trans form isomer of benzhydryl 7-[2-(5-amino-1,2,4-thiadiazol-3-yl)-2-ethoxyiminoacetamido]-3-[2-(3-pyridyl)vinyl]-3-cephem-4-carboxylate (syn isomer) (1.72 g).

trans isomer

IR (Nujol): 1765, 1670 cm$^{-1}$.

NMR δ (DMSO-d$_6$): 1.29 (3H, t, J=7.0 Hz), 3.93 (2H, q, J=18.0 Hz), 4.20 (2H, q, J=7.0 Hz), 5.29 (1H, d, J=5.0 Hz), 5.92 (1H, dd, J=5.0 Hz, 8.0 Hz), 6.98 (1H, d, J=17.0 Hz), 7.00–7.58 (13H, m), 7.03 (1H, s), 8.33–8.51 (2H, m), 9.51 (1H, d, J=8 Hz).

cis isomer

IR (Nujol): 1765, 1670 cm$^{-1}$.

NMR δ (DMSO-d$_6$): 1.24 (3H, t, J=7.0 Hz), 3.45 (2H, q, J=18.0 Hz), 4.19 (2H, q, J=7.0 Hz), 5.32 (1H, d,

J=5.0 Hz), 5.97 (1H, dd, J=5.0 Hz, 8.0 Hz), 6.50 (2H, s), 6.81 (1H, s), 7.14–7.70 (12H, m), 8.34–8.53 (2H, m), 9.66 (1H, d, J=8.0 Hz).

PREPARATION 10

The following compound was obtained according to a similar manner to that of Preparation 1-(7).

7-[2-(5-Amino-1,2,4-thiadiazol-3-yl)-2-ethoxyiminoacetamido]-3-[2-(3-pyridyl)vinyl]-3-cephem-4-carboxylic acid (syn isomer) (trans isomer).

IR (Nujol): 3400, 3250, 1760, 1670, 1655, 1620 cm$^{-1}$.

NMR δ (DMSO-d$_6$): 1.28 (3H, t, J=7.0 Hz), 3.88 (2H, q, J=18.0 Hz), 4.20 (2H, q, J=7.0 Hz), 5.25 (1H, d, J=4.0 Hz), 5.85 (1H, dd, J=4.0 Hz, 8.0 Hz), 7.01 (1H, d, J=17.0 Hz), 7.21–8.24 (3H, m), 8.32–8.75 (2H, m), 9.57 (1H, d, J=8.0 Hz).

PREPARATION 11

(1) Nicotinaldehyde (1.28 g) was added to a solution of }4-benzhydryloxycarbonyl-7-[(5-benzhydryloxycarbonyl-5-benzamido)valeramido]-3-cephem-3-ylmethyl} triphenylphosphonium iodide (4.8 g) in a mixture of N,N-dimethylformamide (48 ml) and ethanol (4.8 ml). The mixture was stirred at ambient temperature for 3.5 hours. To the reaction mixture were added water (300 ml) and ethyl acetate (300 ml). The separated organic layer was washed with brine, and dried over magnesium sulfate. The crude product obtained by concentration was purified by silica gel column chromatography using a mixture of acetone and dichloromethane (1:1 V/V) as an eluent. The fraction containing the desired compound was evaporated to give benzhydryl 7-(5-benzhydryloxycarbonyl-5-benzamidovaleramido)-3-[2-(3-pyridyl)vinyl]-3-cephem-4-carboxylate (cis-trans mixture) (1.25 g).

NMR (DMSO-d$_6$, δ): 1.83 (4H, m), 2.33 (2H, m), 4.63 (1H, m), 5.25 (1H, d, J=5 Hz), 5.83 (1H, dd, J=5 Hz, 8 Hz), 6.33–8.17 (36H, m), 8.45 (2H, m), 8.82 (1H, d, J=8 Hz), 8.95 (1H, d, J=8 Hz).

(2) To a suspension of pyridine-phosphorus pentachloride complex prepared from pyridins (4.7 g) and phosphorus pentachloride (12.5 g) in dichloromethane (90 ml) was added benzhydryl 7-(5-benzhydryloxycarbonyl-5-benzamidovaleramido)-3-[2-(3-pyridyl)vinyl]-3-cephem-4-carboxylate (cis-trans mixture) (17.7 g) under ice-cooling and stirring. The mixture was stirred at the same temperature for 30 minutes. Methanol (5.7 ml) was added to the resulting solution at −15° to −10° C. and poured into water (300 ml). The separated aqueous layer was washed successively with methylene chloride and diisopropyl ether, and the aqueous layer was adjusted to pH 5.5 with 20% aqueous sodium hydroxide. The precipitate was collected by filtration, washed with water and dried over phosphorus pentoxide under reduced pressure to give benzhydryl 7-amino-3-[2-(3-pyridyl)vinyl)-3-cephem-4-carboxylate(cis-trans mixture) (6.9 g).

IR (Nujol): 3300, 1760, 1710 cm$^{-1}$.

NMR (DMSO-d$_6$, δ): 3.87 (2H, m), 4.90 (1H, d, J=5 Hz), 5.15 (1H, d, J=5 Hz), 7.0–7.80 (15H, m), 8.43 (2H, m).

PREPARATION 12

The following compounds were obtained according to a similar manner to that of Preparation 1-(7).

(1) 7-[2-Methoxyimino-2-(5-amino-1,2,4-thiadiazol-3-yl)acetamido]-3-[2-(3-pyridyl)vinyl]-3-cephem-4-carboxylic acid, (syn isomer) (cis-trans mixture).

IR (Nujol): 3270, 3150, 1765, 1670, 1610, 1530 cm$^{-1}$.

NMR (DMSO-d$_6$, δ): 3.37 (2H, ABq, J=18 Hz), 3.90 (3H, s), 5.22 (1H, d, J=5 Hz), 5.83 (1H, dd, J=5 Hz, 8 Hz), 6.35–7.85 (4H, m), 8.47 (2H, m), 9.57 (1H, d, J=8 Hz).

(2) 7-[2-Ethoxyimino-2-(2-aminothiazol-4-yl)-acetamido]-3-[2-(3-pyridyl)vinyl]-3-cephem-4-carboxylic acid (syn isomer) (cis-trans mixture).

IR (Nujol): 3300, 1770, 1670, 1610, 1530 cm$^{-1}$.

NMR (DMSO-d$_6$, δ): 1.20 (3H, t, J=7 Hz), 3.37 (2H, ABq, J=18 Hz), 4.10 (2H, q, J=7 Hz), 5.23 (1H, d, J=8 Hz), 5.80 (1H, dd, J=5 Hz, 8 Hz), 6.37–7.87 (4H, m), 6.70 (1H, s), 8.43 (2H, m), 9.60 (1H, d, J=8 Hz).

(3) 7-[2-Propargyloxyimino-2-(2-aminothiazol-4-yl)acetamido]-3-[2-(3-pyridyl)vinyl]-3-cephem-4-carboxylic acid (syn isomer) (cis-trans mixture).

IR (Nujol): 3250, 1765, 1670, 1610, 1330 cm$^{-1}$.

NMR (DMSO-d$_6$, δ): 3.35 (2H, ABq, J=18 Hz), 3.35 (1H, m), 4.70 (2H, m), 5.23 (1H, d, J=5 Hz), 5.80 (1H, dd, J=5 Hz, 8 Hz), 6.50–7.80 (5H, m), 8.47 (2H, m), 9.67 (1H, d, J=8 Hz).

(4) 7-Formamido-3-[2-(3-pyridyl)vinyl]-3-cephem-4-carboxylic acid (cis-trans mixture).

IR (Nujol): 1760, 1665, 1600 cm$^{-1}$.

NMR (DMSO-d$_6$, δ): 3.93$^{3.41}$} 2H, each q, J=18.0 Hz, 5.22 (1H, d, J=5.0 Hz), 5.82 (1H, dd, J=5.0 Hz, 8.0 Hz), 6.61 (0.5H, s), 7.02 (0.75H, d, J=17.0 Hz), 7.27–7.60 (1H, m), 7.60 (0.75H, d, J=17.0 Hz), 7.68–8.07 (1H, m), 8.37–8.80 (2H, m), 9.11 (1H, d, J=8.0 Hz).

(5) 7-(2-m-Hydroxyphenyl-2-methoxyiminoacetamido)-3-[2-(3-pyridyl)vinyl]-3-cephem-4-carboxylic acid (cis-trans mixture).

IR (Nujol): 3150, 1770, 1678 cm$^{-1}$.

NMR (DMSO-d$_6$, δ): 3.8 (2H, m), 4.0 (3H, s), 5.26 (1H, d, J=4 Hz), 5.90 (1H, dd, J=4 Hz, 8 Hz), 6.7–8.0 (8H, m), 8.50 (2H, m), 9.77 (1H, d, J=8 Hz).

(6) 7-[2-(5-Amino-1,2,4-thiadiazol-3-yl)-2-carboxymethoxyiminoacetamido]-3-[2-(3-pyridyl)vinyl]-3-cephem-4-carboxylic acid (syn isomer) (cis-trans mixture).

IR (Nujol): 3300, 1770, 1674, 1620 cm$^{-1}$.

NMR (D$_2$O-NaHCO$_3$, δ): 3.70 (2H, m), 4.75 (2H, s), 5.30 (1H, d, J=5 Hz), 5.90 (1H, d, J=5 Hz), 6.5–7.8 (4H, m), 8.40 (2H, m).

PREPARATION 13

The following compounds were obtained according to a similar manner to that of Preparation 1-(6).

(1) Benzhydryl 7-[2-propargyloxyimino-2-(2-aminothiazol-4-yl)acetamido]-3-[3-pyridyl)vinyl]-3-cephem-4-carboxylate (syn isomer) (cis-trans mixture).

IR (Nujol): 3250, 1780, 1710, 1670, 1610, 1540 cm$^{-1}$.

NMR (DMSO-d$_6$, δ): 3.50 (2H, ABq, J=18 Hz), 3.50 (1H, m), 4.73 (2H, m), 5.35 (1H, d, J=5 Hz), 5.87 (1H, dd, J=5 Hz, 8 Hz), 6.40–7.73 (15H, m), 8.43 (2H, m), 9.77 (1H, d, J=8 Hz).

(2) Benzhydryl 7-[2-ethoxyimino-2-(2-aminothiazol-4-yl)acetamido]-3-[2-(3-pyridyl)vinyl]-3-cephem-4-carboxylate (syn isomer) (cis-trans mixture).

IR (Nujol): 3200, 1770, 1720, 1670, 1610, 1520 cm$^{-1}$.

NMR (DMSO-d$_6$, δ): 1.23 (3H, s), 3.43 (2H, ABq, J=18 Hz), 4.13 (2H, q, J=7 Hz), 5.33 (1H, d, J=5 Hz), 5.88 (1H, dd, J=5 Hz, 8 Hz), 6.37–7.87 (5H, m), 8.38 (1H, m), 9.62 (1H, d, J=8 Hz).

PREPARATION 14

The following compounds were obtained according to a similar manner to that of Preparation 2-(5).

(1) Benzhydryl 7-[2-allyloxyimino-2-(5-amino-1,2,4-thiadiazol-3-yl)acetamido]-3-[2-(3-pyridyl)vinyl]-3-cephem-4-carboxylate (syn isomer) (cis-trans mixture).

IR (Nujol): 1770, 1720, 1670 cm$^{-1}$.

(2) Benzhydryl 7-[2-propargyloxyimino-2-(2-formamidothiazol-4-yl)acetamido]-3-[2-(3-pyridyl)vinyl]-3-cephem-4-carboxylate (syn isomer) (cis-trans mixture).

IR (Nujol): 3200, 1770, 1710, 1670, 1535 cm$^{-1}$.

NMR (DMSO-$d_6$, δ): 3.17–4.17 (3H, m), 5.08 (2H, m), 5.13 and 5.32 (1H, d, J=5 Hz), 5.80 and 6.0 (1H, dd, J=5 Hz, 8 Hz), 6.4–7.77 (15H, m), 8.37 (1H, s), 8.47 (2H, m), 9.80 (1H, d, J=8 Hz).

(3) Benzhydryl 7-[2-methoxyimino-2-(5-amino-1,2,4-thiadiazol-3-yl)acetamido]-3-[2-(3-pyridyl)vinyl]-3-cephem-4-carboxylate (syn isomer) (cis-trans mixture).

IR (Nujol): 3150, 1760, 1720, 1660, 1520 cm$^{-1}$.

NMR (DMSO-$d_6$, δ): 3.90 (2H, ABq, J=18 Hz), 5.28 (1H, d, J=5 Hz), 5.92 (1H, dd, J=5 Hz, 8 Hz), 6.37–7.90 (15H, m), 8.37 (2H, m), 9.62 (1H, d, J=8 Hz).

(4) Benzhydryl 7-[2-ethoxyimino-2-(2-formamidothiazol-4-yl)acetamido]-3-[2-(3-pyridyl)vinyl]-3-cephem-4-carboxylate (syn isomer) (cis-trans mixture).

IR (Nujol): 3150, 1780, 1720, 1660, 1550 cm$^{-1}$.

NMR (DMSO-$d_6$, δ): 1.2 (3H, t, J=7 Hz), 3.40 (2H, ABq, J=18 Hz), 4.12 (2H, q, J=7 Hz), 5.30 (1H, d, J=5 Hz), 5.92 (1H, dd, J=5 Hz, 8 Hz), 6.37–7.87 (17H, m), 8.40 (2H, m), 9.70 (1H, d, J=8 Hz).

(5) Benzhydryl 7-{2-(m-hydroxyphenyl)-2-methoxyiminoacetamido}-3-[2-(3-pyridyl)vinyl]-3-cephem-4-carboxylate (syn isomer) (cis-trans mixture).

IR (Nujol): 1780, 1720, 1670 cm$^{-1}$.

NMR (DMSO-$d_6$, δ): 3.7 (2H, m), 3.95 (3H, s), 5.03 (1H, d, J=5 Hz), 6.0 (1H, dd, J=5 Hz, 8 Hz), 6.6–7.6 (19H, m), 8.45 (2H, m), 9.80 (1H, d, J=8 Hz).

(6) Benzhydryl 7-[2-(5-amino-1,2,4-thiadiazol-3-yl)-2-tert-butoxycarbonylmethoxyiminoacetamido]-3A-[2-(3-pyridyl)vinyl]-3-cephem-4-carboxylate (syn isomer) (cis-trans mixture).

IR (Nujol): 3350, 1780, 1720, 1683 cm$^{-1}$.

NMR (DMSO-$d_6$, δ): 1.43 (9H, s), 3.67 (2H, m), 4.70 (2H, s), 5.37 (1H, d, J=5 Hz), 6.00 (1H, dd, J=5 Hz, 8 Hz), 6.6–7.6 (7H, m), 8.45 (2H, m), 9.70 (1H, d, J=8 Hz).

PREPARATION 15

Trifluoroacetic acid (2.6 ml) was added to a suspension of benzhydryl 7-[2-allyloxyimino-2-(5-amino-1,2,4-thiadiazol-3-yl)acetamido]-3-[2-(3-pyridyl)vinyl]-3-cephem-4-carboxylate (syn isomer) (cis-trans mixture) (2.3 g) and anisole (1.5 ml) in dichloromethane (11 ml) at ambient temperature and stirred for 1.5 hours at the same temperature. To the resulting solution was added diisopropyl ether (50 ml) and stirred. The precipitate was collected by filtration, washed with diisopropyl ether and then was added to a mixture of ethyl acetate and water. The mixture was adjusted to pH 8 with 20% potassium carbonate. The separated aqueous layer was adjusted to pH 3.5 with 10% hydrochloric acid under ice-cooling. The precipitate was filtered and washed with water. To the precipitate was added water and the mixture was adjusted to pH 5.0 with saturated aqueous sodium bicarbonate. The insoluble substance was filtered off. The filtrate was subjected to column chromatography on macroporous non-ionic adsorption resin "Diaion HP-20" (Trademark: prepared by Mitsubishi Chemical Industries) and eluted with 15% aqueous solution of isopropyl alcohol. The fraction containing the object compound was concentrated and lyophilized to give sodium 7-[2-allyloxyimino-2-(5-amino-1,2,4-thiadiazol-3-yl)acetamido]-3-[2-(3-pyridyl)-vinyl]-3-cephem-4-carboxylate (syn isomer) (0.5 g).

IR (Nujol): 3250, 1760, 1660, 1610 cm$^{-1}$.

NMR (DMSO-$d_6$, δ): 3.73 (2H, broad s), 4.66 (4H, m), 5.06–5.56 (3H, m), 5.63–6.60 (2H, m), 7.06 (1H, d, J=17.0 Hz), 7.29–8.06 (3H, m), 8.40–8.79 (2H, m), 9.61 (1H, d, J=8.0 Hz).

PREPARATION 16

Trifluoroacetic acid (15.2 ml) was added to a suspension of benzhydryl 7-amino-3-[2-(3-pyridyl)vinyl]-3-cephem-4-carboxylate (cis-trans mixture) (8.0 g) and anisole (7.4 ml) in dichloromethane (40 ml) at ambient temperature and the mixture was stirred for 1.5 hours at the same temperature. To the resulting solution was added diisopropyl ether (200 ml) and stirred. The precipitate was collected by filtration and washed with diisopropyl ether. The precipitate was added to a mixture of water and ethyl acetate and the mixture was adjusted to pH 7 with 20% potassium carbonate. The separated aqueous layer was adjusted to pH 4.5 with 10% hydrochloric acid under ice-cooling. The precipitate, whose main component was the desired trans isomer, was filtered off and added to water. The mixture was adjusted to pH 7.0 with saturated aqueous sodium bicarbonate. After removal of an insoluble substance, the aqueous filtrate was adjusted to pH 4.5 with 10% hydrochloric acid under ice-cooling. The resulting precipitate was filtered, washed with ice-cooled water and dried over phosphorus pentoxide in vacuo to give 7-amino-3-[2-(3-pyridyl)vinyl]-3-cephem-4-carboxylic acid (trans isomer) (1.9 g.).

IR (Nujol): 3150, 1790, 1670, 1610 cm$^{-1}$.

NMR ($D_2O$+DCl, δ): 4.03 (2H, s), 5.28 (1H, d, J=5.0 Hz), 5.45 (1H, d, J=5.0 Hz), 7.17 (1H, d, J=17.0 Hz), 7.85 (1H, d, J=17.0 Hz), 7.94–8.25 (1H, m), 8.65–9.00 (3H, m).

PREPARATION 17

Trifluoroacetic acid (18.3 ml) was added to a suspension of benzhydryl 7-[2-(5-amino-1,2,4-thiadiazol-3-yl)-2-ethoxyiminoacetamido]-3-[2-(3-pyridyl)vinyl]-3-cephem-4-carboxylate (syn isomer) (cis-trans mixture) (16.4 g) and anisole (10.7 ml) in dichloromethane (65 ml) at ambient temperature and stirred for 1.5 hours at the same temperature. To the reaction mixture was added diisopropyl ether (300 ml) under stirring. The resulting precipitate was collected by filtration and washed with diisopropyl ether. The precipitate was added to a mixture of ethyl acetate (100 ml) and water (300 ml) and the mixture was adjusted to pH 8 with 20% potassium carbonate. The separated aqueous layer was adjusted to pH 3.5 with 10% hydrochloric acid under ice-cooling. The precipitate, whose main component was the disired trans isomer, was filtered off and added to water (300 ml). The solution was adjusted to pH 7.5 with saturated aqueous sodium bicarbonate. After removal of the insoluble substance by filtration, the filtrate was adjusted to pH 3.5 with 2N-hydrochloric acid under ice-cooling. The precipitate was filtered, washed with ice-cooled water and dried over phosphorus pentoxide in vacuo to give 7-[2-(5-amino-1,2,4-thiadiazol-3-yl)-2-ethoxyiminoacetamido]-3-[2-(3-pyridyl)vinyl]-3-cephem-4-carboxylic acid (syn isomer) (trans isomer) (5.2 g). The filtrate and the washings were combined and the resultant solution was subjected to column chromatography on macroporous non-ionic adsorption resin "Diaion HP-20" and eluted with 30% aqueous solution of isopropyl alcohol. The fraction containing the object compound was concentrated and lyophilized to give 7-[2-(5-amino-1,2,4-thiadiazol-3-yl)-2-ethoxyiminoacetamido]-3-[2-(3-pyridyl)vinyl]-3-cephem-4-carboxylic acid (syn isomer) (cis isomer) (3.7 g).

trans isomer

IR (Nujol): 3400, 3250, 1760, 1670, 1655, 1620 cm$^{-1}$.

NMR (DMSO-d$_6$, δ): 1.28 (3H, t, J=7.0 Hz), 5.25 (1H, d, J=4.0 Hz), 5.85 (1H, dd, J=4.0 Hz, 8.0 Hz), 7.01 (1H, d, J=17.0 Hz), 7.21–8.24 (3H, m), 8.32–8.75 (2H, m), 9.57 (1H, d, J=8.0 Hz).

cis isomer

IR (Nujol): 3250, 1770, 1680, 1610, 1520 cm$^{-1}$.

NMR (DMSO-d$_6$, δ): 1.18 (3H, t, J=7.0 Hz), 3.67 (2H, m), 4.17 (2H, q, J=7.0 Hz), 5.22 (1H, d, J=5.0 Hz), 5.82 (1H, dd, J=5.0 Hz, 8.0 Hz), 6.57 (2H, s), 7.10–7.88 (2H, m), 8.47 (2H, m), 9.58 (1H, d, J=8 Hz).

PREPARATION 18

The following compounds were obtained according to a similar manner to that of Preparation 5-(2).

(1) (4-Benzhydryloxycarbonyl-7-formamido-3-cephem-3-ylmethyl)triphenylphosphonium iodide.

IR (Nujol): 1785, 1680 (br) cm$^{-1}$.

(2) (4-Benzhydryloxycarbonyl-7-(p-nitrobenzamido)-3-cephem-4-ylmethyl]triphenylphosphonium iodide.

IR (Nujol): 1780, 1715, 1670, 1605 cm$^{-1}$.

NMR (DMSO-d$_6$, δ): 1.43 (9H, s), 3.22–4.30 (2H, m), 5.23 (1H, d, J=5.0 Hz), 5.44–5.78 (1H, m), 6.54 (1H, s), 6.71 (0.5H, d, J=0.5H), 7.04–7.81 (13.5H, m), 8.53 (2H, m).

(4) Benzhydryl 7-acetamido-3-[2-(3-pyridyl)vinyl]-3-cephem-4-carboxylate (cis-trans mixture).

IR (Nujol): 1775, 1720, 1670 cm$^{-1}$.

NMR (DMSO-d$_6$, δ): 1.95 (3H, s), {3.93$^{3.47}$} Total 2H, q, J=17.0 Hz),$^{m)}$ 5.26 (1H, d, J=4.0 Hz), 5.81 (1H, dd, J=4.0 Hz, 8.0 Hz), 6.51 (0.5H, s), 6.77 (0.75H, d, J=17.0 Hz), 6.87 (1H, s), 7.07–7.90 (12.75H, m), 8.36–8.56 (2H, m), 8.94 (1H, d, J=8.0 Hz).

(5) Benzhydryl 7-(p-nitrobenzamido)-3-[2-(3-pyridyl)vinyl]-3-cephem-4-carboxylate (cis-trans mixture).

IR (Nujol): 1780, 1720, 1665, 1600 cm$^{-1}$.

NMR (DMSO-d$_6$, δ): 3.33–4.20 (2H, m), 5.40 (1H, d, J=4.0 Hz), 6.02 (1H, dd, J=4.0 Hz, 8.0 Hz), 6.56 (0.5H, s), 6.76 (0.75H, d, J=0.75), 7.09–7.77 (13.75H, m), 8.14 (2H, d, J=8.0 Hz), 8.37 (2H, d, J=8.0 Hz), 8.46 (2H, m), 9.89 (1H, d, J=8.0 Hz).

(3) (4-Benzhydryloxycarbonyl-7-acetamido-3-cephem-3-ylmethyl)triphenylphosphonium iodide.

IR (Nujol): 1770, 1710, 1670 cm$^{-1}$.

NMR (DMSO-d$_6$, δ): 1.94 (3H, s), 3.58 (2H, m), 4.82–5.43 (3H, m), 5.73 (1H, dd, J=5.0 Hz), 8.0 Hz), 6.31 (1H, s), 7.31 (10H, s), 7.52–8.03 (15H, m), 8.86 (1H, d, J=8.0 Hz).

PREPARATION 19

The following compounds were obtained according to a similar manner to that of Preparation 5-(3).

(1) Benzhydryl 7-formamido-3-[2-(3-pyridyl)vinyl]-3-cephem-4-carboxylate (cis-trans mixture).

| IR (NuJol): | 1770, |
| | 1670 |
| | cm$^{-1}$ |

| NMR (DMSO-d$_6$, δ): | 3.12–3.86 | m) |
| | | 2H, |
| | 3.96 | q, J = 18.0Hz), |

5.30 (1H, d, J = 5.0Hz), 5.90 (1H, dd, J = 5.0Hz, 8.0Hz), 6.53 (0.7H, s), 6.83–7.94 (14.3H, m), 8.23 (1H, s), 8.47 (2H, m), 9.16 (1H, d, J = 8.0Hz)

(2) Benzhydryl 7-formamido-3-[2-(3-pyridyl)vinyl]-3-cephem-4-carboxylate (cis-trans mixture).

| IR (Nujol): | 1770, |
| | 1670 |
| | cm$^{-1}$ |

| NMR (DMSO-d$_6$, δ): | 3.12–3.86 (m | ) Total |
| | 3.96 (q, J = 18.0Hz, | ) 2H |

5.30 (1H, d, J = 5.0Hz), 5.90 (1H, dd, J = 5.0Hz, 8.0Hz), 6.53 (0.5H, s), 6.83–7.94 (14.5H, m), 8.23 (1H, s), 8.47 (2H, m), 9.19 (1H, d, J = 8.0Hz)

(3) Benzhydryl 7-t-butoxycarbonylamino-3-[2-(3-pyridyl)vinyl]-3-cephem-4-carboxylate (cis-trans mixture).

IR (Nujol): 1780, 1710 cm$^{-1}$.

PREPARATION 20

The following compounds were obtained according to a similar manner to that of Preparation 2-(5).

(1) Benzhydryl 7-[D(−)-2-(4-ethyl-2,3-dioxo-1-piperazinecarboxamido)-2-(phenyl)acetamido]-3-[2-(3-pyridyl)vinyl]-3-cephem-4-carboxylate (cis-trans mixture).

IR (Nujol): 3270, 1780, 1710, 1670, 1500 cm$^{-1}$.

NMR (DMSO-d$_6$, δ): 1.07 (3H, t, J=7 Hz), 3.20–4.17 (8H, m), 5.17 (1H, d, J=5 Hz), 5.65 (1H, d, J=7 Hz), 5.82 (1H, dd, J=5 Hz, 8 Hz) 6.50 (1H, m), 6.82 (1H, s), 7.0–7.83 (16H, m), 8.45 (2H, m), 9.53 (1H, d, J=7 Hz), 9.83 (1H, d, J=8 Hz).

(2) Benzhydryl 7-[D(−)-2-(4-ethyl-2,3-dioxo-1-piperazinecarboxamido)-2-(4-hydroxyphenyl)acetamido]-3-[2-(3-pyridyl)vinyl]-3-cephem-4-carboxylate (cis-trans mixture).

IR (Nujol): 3250, 1780, 1710, 1680, 1600, 1500 cm$^{-1}$.

NMR (DMSO-d$_6$, δ): 1.08 (3H, t, J=7 Hz), 3.17–4.10 (8H, m), 5.17 (1H, d, J=5 Hz), 5.52 (1H, d, J=7 Hz), 5.83 (1H, dd, J=5 Hz, 8 Hz), 6.57 (1H, d, J=13 Hz), 6.82 (1H, s), 7.0–7.67 (17H, m), 8.45 (2H, m), 9.42 (1H, d, J=7 Hz), 9.73 (1H, d, J=8 Hz).

PREPARATION 21

The following compounds were obtained according to a similar manner to that of Preparation 1-(7).

(1) 7-[D(−)-2-(4-ethyl-2,3-dioxo-1-piperazinecarboxamido)-2-(phenyl)acetamido]-3-pyridyl)vinyl]-3-cephem-4-carboxylic acid (cis-trans mixture).

IR (Nujol): 3270, 1770, 1710, 1670, 1510 cm$^{-1}$.

NMR (DMSO-d$_6$, δ): 1.10 (3H, t, J=7 Hz), 3.42 (2H, q, J=7 Hz), 3.32–4.10 (6H, m), 5.15 (1H, d, J=5 Hz), 5.67 (1H, d, J=7 Hz), 5.68 (1H, dd, J=5 Hz, 8 Hz), 6.58 (1H, s), 7.10–8.10 (8H, m), 8.58 (2H, m), 9.55 (1H, d, J=7 Hz), 9.90 (1H, d, J=8 Hz).

(2) 7-[D(−)-2-(4-ethyl-2,3-dioxo-1-piperazinecarboxamido)-2-(4-hydroxyphenyl)acetamido]-3-[2-(3-pyridyl)vinyl]-3-cephem-4-carboxylic acid (cis-trans mixture).

IR (Nujol): 3250, 1770, 1710, 1670, 1610, 1510 cm$^{-1}$.

NMR (DMSO-d$_6$, δ): 1.10 (3H, t, J=7 Hz), 3.40 (2H, q, J=7 Hz), 3.17-4.17 (6H, m), 5.13 (1H, d, J=5 Hz), 5.52 (1H, d, J=7 Hz), 5.77 (1H, dd, J=5 Hz, 8 Hz), 7.0 (4H, ABq, J=7 Hz), 6.5-8.1 (4H, m), 8.55 (2H, m), 9.40 (1H, d, J=7 Hz), 9.75 (1H, d, J=8 Hz).

PREPARATION OF THE OBJECT COMPOUNDS OF THE PRESENT INVENTION

EXAMPLE 1

A mixture of 7-amino-3-[2-(1-methyl-3-pyridinio)-vinyl]-3-cephem-4-carboxylate dihydrochloride (cis-trans mixture) (0.39 g) and N-(trimethylsilyl)acetamide (0.92 g) in tetrahydrofuran (10 ml) was stirred at ambient temperature for 20 minutes to give a clear solution. To the solution was added 2-ethoxyimino-2-(5-amino-1,2,4-thiadiazol-3-yl)acetylchloride (syn isomer) (0.41 g) at −15~−10° C. and stirred at the same temperature for 30 minutes. Water (10 ml) was added to the resulting solution, and separated aqueous layer was adjusted to pH 3.5 with 5% aqueous sodium bicarbonate solution. The solution was subjected to column chromatography on macroporous non-ionic adsorption resin "Diaion HP-20" [Trademark: prepared by Mitsubishi Chemical Industries] and eluted with 10% aqueous solution of iso-propyl alcohol. Fraction containing the object compound was concentrated and lyophilized to give 7-[2-(5-amino-1,2,4-thiadiazol-3-yl)-2-ethoxyiminoacetamido]-3-[2-(1-methyl-3-pyridinio)vinyl]-3-cephem-4-carboxylate (syn isomer) (cis-trans mixture) (0.15 g).

IR (Nujol): 1765, 1660, 1610 cm$^{-1}$.

NMR (D$_2$O, δ): 1.33 (3H, t, J=7.0 Hz), 3.42 and 3.77 (Total 2H, each q, J=18.0 Hz and broad s), 4.30 (2H, q, J=7.0 Hz), 4.31 (3H, s), 5.26 (1H, d, J=4.0 Hz), 5.80 (1H, d, J=4.0 Hz), 6.55 (1H, s), 6.66 (0.5H, d, J=17.0 Hz), 7.43 (0.5H, d, J=17 Hz), 7.64-8.73 (4H, m).

EXAMPLE 2

The following compounds were obtained according to a similar manner to that of Example 1.

(1) 7-phenylacetamido-3-[2-(1-methyl-3-pyridinio)-vinyl]-3-cephem-4-carboxylate methanesulfonate (cis-trans mixture).

IR (Nujol): 3200, 1750, 1650, 1510 cm$^{-1}$.

(2) 7-phenylacetamido-3-[2-(1-methyl-3-pyridinio)-vinyl]-3-cephem-4-carboxylate (cis-trans mixture).

IR (Nujol): 3200, 1770, 1660, 1600, 1540 cm$^{-1}$.

EXAMPLE 3

A mixture of benzhydryl 7-phenylacetamido-3-[2-(1-methyl-3-pyridinio)vinyl]-3-cephem-4-carboxylate iodide (cis-trans mixture)(1.8 g) and trifluoroacetic acid (2.8 g) and anisole (1.06 g) in dichloromethane (8 ml) was stirred at ambient temperature for an hour. The reaction mixture was dropwise added to di-isopropyl ether and the resultant precipitate was filtered. The precipitate was suspended in water and adjusted to pH 7.0 with 20% aqueous potassium carbonate. The insoluble substance was filtered off and the filtrate was acidified to pH 2.0 with 10% hydrochloric acid. The solution was subjected to column chromatography on macroporous non-ionic adsorption resin "Diaion HP-20" and eluted with 20% aqueous solution of isopropyl alcohol. The fraction containing the object compound was concentrated and lyophilized to give 7-phenylacetamido-3-[2-(1-methyl-3-pyridinio)vinyl]-3-cephem-4-carboxylate (cis-trans mixture)(0.3 g).

IR (Nujol): 3200, 1770, 1660, 1600, 1540 cm$^{-1}$.

NMR δ (DMSO-d$_6$): 3.47 (2H, q, J=18 Hz), 3.55 (2H, s), 4.35 (3H, s), 5.18 (1H, d, J=5 Hz), 5.60 (1H, dd, J=5, 8 Hz), 6.25 (0.5H, d, J=7 Hz), 6.30 (1H, s), 7.0-7.6 (0.5H, m), 7.27 (5H, s), 7.77-8.67 (2H, m), 8.90 (2H, m), 9.13 (1H, d, J=8 Hz).

EXAMPLE 4

The following compounds were obtained according to a similar manner to that of Example 3.

(1) 7-phenylacetamido-3-[2-(1-methyl-3-pyridinio)-vinyl]-3-cephem-4-carboxylate methanesulfonate (cis-trans mixture).

IR (Nujol): 3200, 1750, 1650, 1510 cm$^{-1}$.

(2) 7-[2-(5-amino-1,2,4-thiadiazol-3-yl)-2-ethoxyiminoacetamido]-3-[2-(1-methyl-3-pyridinio)vinyl]-3-cephem-4-carboxylate (cis-trans mixture).

IR (Nujol): 1765, 1660, 1610 cm$^{-1}$.

(3) 7-amino-3-[2-(1-methyl-3-pyridinio)vinyl]-3-cephem-4-carboxylate dihydrochloride (cis-trans mixture).

IR (Nujol): 1780, 1700 cm$^{-1}$.

EXAMPLE 5

(1) A mixture of 7-phenylacetamido-3-[2-(3-pyridyl)-vinyl]-3-cephem-4-carboxylic acid trifluoroacetate (cis-trans mixture)(0.5 g) and methyl methanesulfonate (0.13 g) in tetrahydrofuran (60 ml) was stirred at ambient temperature for 48 hours. The precipitate was collected by filtration and washed with tetrahydrofuran to give 7-phenylacetamido-3-[2-(1-methyl-3-pyridinio)vinyl]-3-cephem-4-carboxylate methanesulfonate (cis-trans mixture)(0.2 g).

IR (Nujol): 3200, 1750, 1650, 1510 cm$^{-1}$.

NMR δ (DMSO-d$_6$): 2.37 (3H, s), 3.53 (2H, s), 3.53 (2H, m), 4.33 (3H, s), 5.20 (1H, dd, J=5 Hz), 5.68 (1H, dd, J=5 Hz, 8 Hz), 7.23 (5H, s), 6.72 (1H, s),7.10 (0.5H, d, J=17 Hz), 7.50 (0.5H, d, J=17 Hz), 8.0-8.7 (2H, m), 8.83 (2H, m), 9.07 (1H, d, J=8 Hz).

(2) 7-phenylacetamido-3-[2-(1-methyl-3-pyridinio)-vinyl]-3-cephem-4-carboxylate methanesulfonate (cis-trans mixture)(0.8 g) was added to water (14 ml). The solution was acidified to pH 2.0 with 10% hydrochloric acid. The solution was subjected to column chromatography on macroporous non-ionic adsorption resin "Diaion HP-20" and eluted with 30% aqueous solution of isopropylalcohol. The fraction containing the object compound was concentrated and lyophilized to give 7-phenylacetamido-3-[2-(1-methyl-3-pyridinio)vinyl]-3-cephem-4-carboxylate (cis-trans mixture)(0.41 g).

IR (Nujol): 3200, 1770, 1660, 1600, 1540 cm$^{-1}$.

NMR δ (DMSO-d$_6$): 3.47 (2H, q, J=18 Hz), 3.55 (2H, s), 4.35 (3H, s), 5.18 (1H, d, J=5 Hz), 5.60 (1H, dd, J=5,8 Hz), 6.25 (0.5H, d, J=17 Hz), 6.30 (1H, s), 7.0-7.6 (0.5H, m), 7.27 (5H, s), 7.77-8.67 (2H, m), 8.90 (2H, m), 9.13 (1H, d, J=8 Hz).

EXAMPLE 6

The following compounds were obtained according to a similar manner to that of Example 5.

(1) 7-[2-(5-amino-1,2,4-thiadiazol-3-yl)-2-ethoxyiminoacetamido]-3-[2-(1-methyl-3-pyridinio)vinyl]-3-cephem-4-carboxylate (syn isomer) (cis-trans mixture).

IR (Nujol): 1765, 1660, 1610 cm$^{-1}$.

(2) 7-amino-3-[2-(1-methyl-3-pyridinio)vinyl]-3-cephem-4-carboxylate dihydrochloride (cis-trans mixture).

IR (Nujol): 1780, 1700 cm$^{-1}$.

43

EXAMPLE 7

To a suspension of 7-phenylacetamido-3-[2-(1-methyl-3-pyridinio)vinyl]-3-cephem-4-carboxylate methanesulfonate (cis-trans mixture)(0.8 g) and dimethylaniline (0.7 g) in dichloromethane (10 ml) was added trimethylsilyl chloride (0.33 g) at 22° to 25° C. and the mixture was stirred at 30° to 35° C. for 2 hours. To the mixture was added phosphorous pentachloride (0.63 g) at −30° to 28° C., and the solution was stirred at −33° to −25° C. for 1.5 hours. 1,3-Butane diol (1.6 ml) was added to the above solution at −28° to −5° C. and stirred for 0° to 5° C. for 30 minutes. The resultant mixture was decanted and the residue was washed with dichloromethane. The residue dissolved in methanol (5 ml) was dropwise added to dichloromethane (40 ml). The resulting precipitate was collected by filtration and washed with dichloromethane to give 7-amino-3-[2-(1-methyl-3-pyridinio)vinyl]-3-cephem-4-carboxylate dihydrochloride (cis-trans mixture) (0.32 g).

IR (Nujol): 1780, 1700 cm$^{-1}$.

NMR $\delta$ ($D_2O$): 3.56 (2H, m), 4.38 (3H, s), 5.27 (2H, m), 6.67–9.00 (6H, m).

EXAMPLE 8

The following compounds were obtained according to a similar manner to those of Example 1, 3 and 5.

(1) 7-[2-(5-Amino-1,2,4-thiadiazol-3-yl)-2-ethoxyiminoacetamido]-3-[2-(1-methyl-3-pyridinio)-vinyl]-3-cephem-4-carboxylate (syn isomer) (trans isomer).

IR (Nujol): 3300, 1765, 1660, 1610 cm$^{-1}$.

NMR $\delta$ ($D_2O$): 1.33 (3H, t, J=7.0 Hz), 3.79 (2H, br s), 4.33 (2H, q, J=7.0 Hz), 4.37 (3H, s), 5.30 (1H, d, J=5.0 Hz), 5.85 (1H, d, J=5.0 Hz), 6.74 (1H, d, J=17.0 Hz), 7.53 (1H, d, J=17.0 Hz), 7.75–8.10 (1H, m), 8.33–8.83 (3H, m).

(2) 7-[2-(5-Amino-1,2,4-thiadiazol-3-yl)-2-ethoxyiminoacetamido]-3-[2-(1-methyl-3-pyridinio)-vinyl]-3-cephem-4-carboxylate (syn isomer) (cis isomer).

IR (Nujol): 1765, 1665, 1600 cm$^{-1}$.

NMR $\delta$ ($D_2O$): 1.33 (3H, t, J=7.0 Hz), 3.48 (2H, q, J=18.0 Hz), 4.33 (2H, q, J=7.0 Hz), 4.34 (3H, s), 5.30 (1H, d, J=5.0 Hz), 5.81 (1H, d, J=5.0 Hz), 6.60 (2H, s), 7.76–8.08 (1H, m), 8.26–8.79 (3H, m).

(3) 7-[2-(5-Amino-1,2,4-thiadiazol-3-yl)-2-ethoxyiminoacetamido]-3-[2-(1-methyl-2-pyridinio)vinyl]-3-cephem-4-carboxylate (syn isomer) (trans isomer).

IR (Nujol): 3300, 1770, 1670, 1630, 1510 cm$^{-1}$.

NMR (DMSO-$d_6$, $\delta$): 1.28 (3H, t, J=7 Hz), 3.32–4.17 (2H, m), 4.10 (2H, q, J=7 Hz), 4.27 (3H, s), 5.22 (1H, d, J=5 Hz), 5.80 (1H, dd, J=5 Hz, 8 Hz), 6.85 (1H, d, J=17 Hz), 7.93–8.67 (4H, m), 8.80 (1H, m), 9.58 (1H, d, J=8 Hz).

(4) 7-[2-(5-Amino-1,2,4-thiadiazol-3-yl)-2-ethoxyiminoacetamido]-3-[2-(1-ethyl-3-pyridinio)vinyl]-3-cephem-4-carboxylate (syn isomer) (trans isomer).

IR (Nujol): 3250, 1765, 1660, 1610 cm$^{-1}$.

NMR ($D_2O$, $\delta$): 1.34 (3H, t, J=7.0 Hz), 1.63 (3H, t, J=7.0 Hz), 3.78 (2H, br. s), 4.35 (2H, q, J=7.0 Hz), 4.30–5.00 (2H, overlap with $D_2O$), 5.32 (1H, d, J=5.0 Hz), 5.87 (1H, d, J=5.0 Hz), 6.73 (1H, d, J=16.0 Hz), 7.53 (1H, d, J=16.0 Hz), 7.77–8.10 (1H, m), 8.33–8.94 (3H, m).

(5) 7-[2-(5-Amino-1,2,4-thiadiazol-3-yl)-2-ethoxyiminoacetamido]-3-[2-(1-ethyl-3-pyridinio)vinyl]-3-cephem-4-carboxylate (syn isomer) (cis isomer).

IR (Nujol): 3250, 1760, 1660, 1600 cm$^{-1}$.

44

NMR ($D_2O$, $\delta$): 1.34 (3H, t, J=7.0 Hz), 1.64 (3H, t, J=7.0 Hz), 3.51 (2H, q, J=18.0 Hz), 4.38 (2H, q, J=7.0 Hz), 4.68 (2H, q, J=7.0 Hz), 5.33 (1H, d, J=5.0 Hz), 5.85 (1H, d, J=5.0 Hz), 6.67 (2H, s), 7.83–8.14 (1H, m), 9.30–8.93 (3H, m).

(6) 7-[2-Methoxyimino-2-(2-aminothiaziol-4-yl)-acetamido]-3-[2-(1-methyl-3-pyridinio)vinyl]-3-cephem-4-carboxylate (syn isomer) (trans isomer).

IR (Nujol): 3280, 1760, 1655, 1610 cm$^{-1}$.

NMR ($D_2O$-DCl, $\delta$): 3.97 (2H, s), 4.11 (3H, s), 4.43 (3H, s), 5.36 (1H, d, J=5.0 Hz), 5.86 (1H, d, J=5.0 Hz), 7.07 (1H, d, J=17.0 Hz), 7.19 (1H, s), 7.77 (1H, d, J=17.0 Hz), 7.99–8.20 (1H, m), 8.48–9.01 (3H, m).

(7) 7-[2-Propargyloxyimino-2-(2-aminothiazol-4-yl)acetamido]-3-[2-(1-methyl-3-pyridinio)vinyl]-3-cephem-4-carboxylate (syn isomer) (cis-trans mixture).

IR (Nujol): 3250, 2100, 1765, 1660, 1605 cm$^{-1}$.

NMR ($D_2O$-DCl, $\delta$): 3.12 (1H, m), {$_{3.98}$$^{3.58}$} Total 2H, m),$^q$, J=18.0 Hz) 4.44 (3H, s), 4.96 (2H, m), 5.36 and 5.41 (total 1H, each d, J=5.0 Hz), 5.81 and 5.87 (Total 1H, each d, J=5.0 Hz), 6.86 (1H, s), 7.09 (0.5H, d, J=17.0 Hz), 7.27 (1H, s), 7.80 (0.5H, d, J=17.0 Hz), 8.00–8.23 (1H, m), 8.34–9.02 (3H, m).

(8) 7-[2-Allyloxyimino-2-(5-amino-1,2,4-thiadiazol-3yl)acetamido]-3-[2-(1-methyl-3-pyridinio)-vinyl]-3-cephem-4-carboxylate (syn isomer) (trans isomer).

IR (Nujol): 3280, 1765, 1660, 1610 cm$^{-1}$.

NMR ($D_2O$-DCl, $\delta$): 3.92 (2H, m), 4.32 (3H, s), 4.93 (2H, d, J=5.0 Hz), 5.17–5.63 (3H, m), 5.75–6.14 (2H, m), 7.06 (1H, d, J=17.0 Hz), 7.71 (1H, d, J=17.0 Hz), 7.95–8.17 (1H, m), 8.44–8.94 (3H, m).

(9) 7-[2-Methoxyimino-2-(m-hydroxyphenyl)-acetamido]-3-[2-(1-methyl-3-pyridinio)vinyl]-3-cephem-4-carboxylate (syn isomer) (cis-trans mixture).

IR (Nujol): 3200, 1770, 1660, 1605 cm$^{-1}$.

NMR (DMSO-$d_6$-DCl, $\delta$): 3.8–4.1 (2H, m), 3.93 (3H, s), 4.40 (3H, s), 5.36 (1H, d, J=5 Hz), 5.90 (1H, d, J=5 Hz), 6.7–7.6 (6H, m), 7.9–9.2 (4H, m).

(10) 7-[2-Carboxymethoxyimino-2-(5-amino-1,2,4-thiadiazol-3-yl)acetamido]-3-[2-(1-methyl-3-pyridinio)-vinyl]-3-cephem-4-carboxylate (syn isomer) (cis-trans mixture).

IR (Nujol): 3300, 1768, 1672, 1616 cm$^{-1}$.

NMR ($D_2O$/NaHCO$_3$, $\delta$): 3.76 (2H, br. s), 4.35 (3H, s), 4.7 (2H, br. s), 5.33 (1H, d, J=5 Hz), 5.86 (1H, d, J=5 Hz), 6.65–7.8 (2H, m), 7.8–8.83 (4H, m).

(11) 7-Formamido-3-[2-(1-methyl-3-pyridinio)vinyl]-3-cephem-4-carboxylate hydriodide (cis-trans mixture).

IR (Nujol): 1770, 1670 (br) cm$^{-1}$.

NMR (DMSO-$d_6$, $\delta$): {$_{3.72}$$^{3.50}$} (Total 2H, m), 4.35 (3H, s), 5.25 (1H, d, J=4.0 Hz), 5.63–5.98 (1H, m), 6.61 (0.75 H, d, J=16.0 Hz), 6.70 (0.5 H, s), 7.35 (0.75 H, d, J=16.0 Hz), 7.87–8.08 (1H, m), 8.12 (1H, s), 8.22–9.20 (3H, m).

EXAMPLE 9

A mixture of 7-formamido-3-[2-(1-methyl-3-pyridinio)vinyl]-3-cephem-4-carboxylate hydriodide (cis-trans mixture) (0.3 g) in methanol (5 ml) and conc. hydrochloric acid (0.2 g) was stirred for 2 hours at ambient temperature. The insoluble material was collected by filtration, washed with methanol to give 7-amino-3-[2-(1-methyl-3-pyridinio)vinyl]-3-cephem-4-carboxylate hydriodide hydrochloride (trans isomer) (0.17 g). To the above filterate was added the isopropyl ether and stirred. The precipitate was collected by filteration to give 7-amino-3-[2-(1-methyl-3-pyridnio)vinyl]-3-cephem-4-carboxylate hydriodide hydrochloride (cis isomer, containing small amount of trans isomer) (90 mg).

trans isomer

IR (Nujol): 1780, 1705 cm$^{-1}$.

NMR (D$_2$O, δ): 3.99 (2H, s), 4.41 (3H, s), 5.25 (1H, d, J=5.0 Hz), 5.43 (1H, d, J=5.0 Hz), 7.05 (1H, d, J=17.0 Hz), 7.75 (1H, d, J=17.0 Hz), 7.96–8.32 (1H, m), 8.49–8.80 (2H, m), 8.90 (1H, s).

cis isomer

IR (Nujol): 1775, 1705 cm$^{-1}$.

NMR (D$_2$O, δ): 3.93 (2H, m), 4.41 (3H, s), 5.20 (1H, d, J=5.0 Hz), 5.46 (1H, d, J=5.0 Hz), 6.86 (2H, s), 7.91–8.18 (1H, m), 8.25–8.98 (3H, m).

EXAMPLE 10

Vilsmeier reagent was prepared from phosphorus oxychloride (0.3 ml) and dimethylformamide (0.3 g) in ethyl acetate (1.2 ml) in usual manner. 2-Methoxyimino-2-(2-trifluoroacetamidothiazol-4-yl)acetic acid (syn isomer)(1.0 g) was added to the stirred suspension of Vilsmeier reagent in tetrahydrofuran (15 ml) under ice-cooling and stirred for 30 minutes at the same temperature to produce an activated acid solution.

7-Amino-3-[2-(1-methyl-3-pyridinio)vinyl]-3-cephem-4-carboxylate hydriodide (trans isomer) (1.2 g) was dissolved to the solution of sodium bicarbonate (0.7 g) in water (10 ml) and acetone (20 ml). To the solution was added the above activated acid solution at −3° to 3° C. and the solution was stirred for 30 minutes under keeping the pH 6.5 to 7.5 with 20% aqueous potassium carbonate. Water and ethyl acetate were added to the reaction mixture containing 7-[2-(2-trifluoroacetamidothiazol-4-yl)-2-methoxyiminoacetamido]-3-[2-(1-methyl-3-pyridinio)vinyl]-3-cephem-4-carboxylate (syn isomer)(trans isomer) and the separated aqueous layer was adjusted to pH 5.0 with 10% hydrochloric acid. Sodium acetate (2.2 g) was added the aqueous layer and a solution was stirred for 18 hours at ambient temperature. The resulting solution was adjusted to pH 4.0 with 10% hydrochloric acid and a solution was subjected to column chromatography on macroporus non-ionic adsorption resin "Diaion HP-20" and eluted with 10% aqueous isopropyl alcohol. The fractions of the object compound was concentrated and freeze-dried to give 7-[2-(2-aminothiazol-4-yl)-2-methoxyiminoacetamido]-3-[2-(1-methyl-3-pyridinio)vinyl]-3-cephem-4-carboxylate (syn isomer) (trans isomer) (0.81 g).

IR (Nujol): 3280, 1760, 1655, 1610 cm$^{-1}$.

NMR (D$_2$O-DCl, δ): 3.97 (2H, s), 4.11 (3H, s), 4.43 (3H, s), 5.36 (1H, d, J=5.0 Hz), 5.86 (1H, d, J=5.0 Hz), 7.07 (1H, d, J=17.0 Hz), 7.19 (1H, s), 7.77 (1H, d, J=17.0 Hz), 7.99–8.20 (1H, m), 8.48–9.01 (3H, m).

What we claim is:

1. New cephem compounds of the formula:

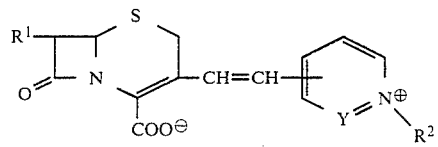

wherein
$R^1$ is carboxylic acylamino,
$R^2$ is lower alkyl, and
Y is CH or N,
and pharmaceutically acceptable salts thereof.

2. A compound of claim 1, wherein $R^1$ is lower alkanoylamino, ar(lower)-alkanoylamino, hydroxy substituted ar(lower)-alkanoylamino having a lower alkoxyimino, amino or acylamino-thiazolyl(lower)alkanoylamino having a lower alkoxyimino, amino or acylaminothiazolyl(lower)alkanoylamino having a lower alkynyloxyimino, aminothiadiazolyl(lower)alkanoylamino having a lower alkoxyimino, aminothiadiazolyl(lower)alkanoylamino having a lower alkenyloxyimino, or aminothiadiazolyl(lower)alkanoylamino having a carboxy(lower)alkoxyimino.

3. Syn isomer of a compound of claim 2, wherein $R^1$ is 2-methoxyimino-2-(2-aminothiazol-4-yl)acetamido, 2-propargyloxyimino-2-(2-aminothiazol-4-yl)acetamido, 2-ethoxyimino-2-(5-amino-1,2,4-thiadiazol-3-yl)-acetamido, 2-allyloxyimino-2-(5-amino-1,2,4-thiadiazol-3-yl)acetamido, 2-carboxymethoxyimino-2-(5-amino-1,2,4-thiadiazol-3-yl)acetamido, or 2-methodyimino-2-(m-hydroxyphenyl)acetamido, and $R^2$ is methyl or ethyl.

4. A compound of claim 3 which is 7-[2-methoxyimino-2-(2-aminothiazol-4-yl)acetamido]-3-[2-(1-methyl-3-pyridinio)vinyl]-3-cephem-4-carboxylate (syn isomer)(trans isomer).

5. A compound of claim 3, which is 7-[2-propargyloxyimino-2-(2-aminothiazol-4-yl)-acetamido]-3-[2-(1-methyl-3-pyridinio)vinyl]-3-cephem-4-carboxylate (syn isomer) (cis-trans mixture).

6. A compound of claim 3, which is selected from the group consisting of:

7-[2-ethoxyimino-2-(5-amino-1,2,4-thiadiazol-3-yl)-acetamido]-3-[2-(1-methyl-3-pyridinio)vinyl]-3-cephem-4-carboxylate (syn isomer) (cis isomer, trans isomer or cis-trans mixture), 7-[2-ethoxyimino-2-(5-amino-1,2,4-thiadiazol-3-yl)-acetamido]-3-[2-(1-methyl-2-pyridinio)vinyl]-3-cephem-4-carboxylate (syn isomer) (trans isomr) and 7-[2-ethoxyimino-2-(5-amino-1,2,4-thiadiazol-3-yl)-acetamido]-3-[2-(1-ethyl-3-pyridinio)vinyl]-3-cephem-4-carboxylate (syn isomer) (cis isomer or trans isomer).

7. A compound of claim 3, which is
7-[2-allyloxyimino-2-(5-amino-1,2,4-thiadiazol-3-yl)acetamido]-3-[2-(1-methyl-3-pyridinio)vinyl]-3-cephem-4-carboxylate (syn isomer) (trans isomer).

8. A compound of claim 3, which is 7-[2-carboxymethoxyimino-2-(5-amino-1,2,4-thiadiazol-3-yl)acetamido]-3-[2-(1-methyl-3-pyridinio)vinyl]-3-cephem-4-carboxylate (syn isomer) (cis-trans mixture).

9. An antimicrobial pharmaceutical composition comprising an effective amount of a compound of claim 1 or pharmaceutically acceptable salt thereof in association with a pharmaceutically acceptable, substantially non-toxic carrier or excipient.

10. A method for producing an antimicrobial pharmaceutical composition which comprises mixing a compound of claim 1 or pharmaceutically acceptable salt thereof as an active ingredient with an inert carrier.

11. A method of treatment of infectious diseases which comprises administering a compound of claim 1 or pharmaceutically acceptable salt thereof to a human being or animal.

12. A cephem compound of the formula:

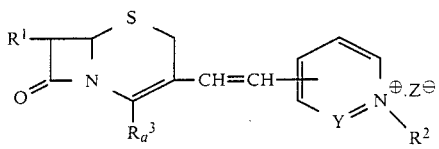
wherein
R¹ is carboxylic acylamino,
R² is lower alkyl,
$R_a^3$ is carboxy or a protected carboxy,
Y is CH or N, and
Z is an acid residue,
and a salt thereof.
* * * * *
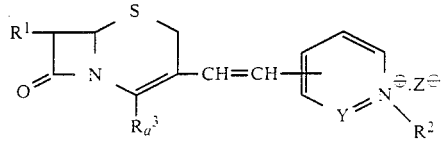
wherein
R¹ is carboxylic acylamino,
R² is lower alkyl,
$R_a^3$ is carboxy or a protected carboxy,
Y is CH or N, and
Z is an acid residue,
and a salt thereof.
* * * * *